US007605127B2

(12) United States Patent
Chan et al.

(10) Patent No.: US 7,605,127 B2
(45) Date of Patent: Oct. 20, 2009

(54) TRUNCATED HEPATOCYTE GROWTH FACTOR VARIANT PROTEIN HGF/NK2

(75) Inventors: Andrew M. L. Chan, Rockville, MD (US); Jeffrey S. Rubin, Rockville, MD (US); Donald P. Bottaro, Kensington, MD (US); Stuart A. Aaronson, New York City, NY (US); Stephen J. Stahl, Bethesda, MD (US); Paul T. Wingfield, Bethesda, MD (US); Vittoria Cioce, New York, NY (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 590 days.

(21) Appl. No.: 10/283,769

(22) Filed: Oct. 30, 2002

(65) Prior Publication Data

US 2003/0124671 A1    Jul. 3, 2003

Related U.S. Application Data

(60) Division of application No. 08/484,841, filed on Jun. 7, 1995, now Pat. No. 6,566,098, which is a continuation-in-part of application No. 08/130,134, filed on Oct. 4, 1993, now abandoned, which is a continuation-in-part of application No. 07/655,502, filed on Feb. 15, 1991, now abandoned, which is a continuation-in-part of application No. 07/582,063, filed on Sep. 14, 1990, now abandoned.

(51) Int. Cl.
*C07K 14/475* (2006.01)
*A61K 38/18* (2006.01)

(52) U.S. Cl. .................................. 514/12; 530/399

(58) Field of Classification Search ................ 530/350, 530/399
See application file for complete search history.

(56) References Cited

U.S. PATENT DOCUMENTS

| 4,959,314 | A | 9/1990 | Mark et al. |
| 4,966,963 | A | 10/1990 | Patroni |
| 5,004,805 | A | 4/1991 | Gohda et al. |
| 5,316,921 | A | 5/1994 | Godowski et al. |
| 5,328,837 | A | 7/1994 | Godowski et al. |

FOREIGN PATENT DOCUMENTS

| EP | 0 246 753 | 11/1987 |
| WO | WO 92/05184 | 4/1992 |
| WO | WO 93/23541 | 11/1993 |
| WO | WO 93/23550 | 11/1993 |
| WO | WO 94/06909 | 3/1994 |

OTHER PUBLICATIONS

Rudinger, In "Peptide Hormones", ed J.A. Parsons, University Park Press, Baltimore, pp. 1-7 (Jun. 1976).
Cunningham et al., "High-resolution epitope mapping of hGH-receptor interactions by alanine-scanning mutagenesis." Science 244(4908):1081-1085 (Jun. 1989).
N.A. Lokker et al., "Structure-Function Analysis of Hepatocyte Growth Factor: Identification of Variants That Lack Mitogenic Activity Yet Retain High Affinity . . .", *The EMBO Journal* 11(7): 2503-2510 (1992).
M. Okigaki et al., "Functional Characterization of Human Hepatocyte Growth Factor Mutants Obtained by Deletion of Structural Domains", *Biochemistry* 31: 9555-9561 (1992).
N.A. Lokker et al., "Generation and Characterization of a Competitive Antagonist of Human Hepatocyte Growth Factor, HGF/NK1", *The Journal of Biological Chemistry* 258(23): 17145-17150 (1993).
G. Hartmann et al., "A Functional Domain in the Heavy Chain of Scatter Factor/Hepatocyte Growth Factor Binds the c-Met Receptor and Induces . . .", *Proc. Natl. Acad. Sci. USA* 89: 11574-11578 (1992).
K. Miyazawa et al., "An Alternatively Processed mRNA Generated from Human Hepatocyte Growth Factor Gene", *Eur. J. Biochem*. 197: 15-22 (1991).
T. Nakamura et al., "Molecular Cloning and Expression of Human Hepatocyte Growth Factor", *Nature* 342: 440-443 (1989).
K. Miyazawa et al., "Molecular Cloning and Sequence Analysis of cDNA for Human Hepatocyte Growth Factor",*Biochem. and Biophys. Res. Comm*. 163(2): 967-973 (1989).
T. Seki et al., "Isolation and Expression of cDNA for Different Forms of Hepatocyte Growth Factor from Human Leukocyte", *Biochem. and Biophys. Res. Comm*. 172(1): 321-327 (1990).
Finch et al., "Human KGF is FGF-Related with Properties of a Paracrine Effector of Epithelial Cell Growth" *Science* 245: 752-755 (Aug. 1989).
Chan et al., "Isoforms of Human HGF and Their Biological Activities", *EXS*, 65: 67-79 (1993).
Chan et al., "Identification of a Competitive HGF Antagonist Encoded by an Alternative Transcript," *Science*, 254: 67-79 (Nov. 1991).
Datar et al., "Process Economics of Animal Cell and Bacterial Fermentations: A Case Study Analysis of Tissue Plasminogen Activator" *Bio/Technology*, 11: 349-355 (Mar. 1993).
Skerra et al., Assembly of A Functional Immunoglobulin $F_v$ Fragment in *Escherichia coli, Science*, 240: 1038-1040 (May 1988).
Matsumoto et al., "Deletion of Kringe Domains or the N-Terminal Hairpin Structure in Hepatocyte Growth Factor Results in Marked Decreases in Related Biological Activities," *Biochemical and Biophysical Research Communications*, 181(2): 691-699 (1991).
Gherardi et al., "Properties and Structure-Function Relationship of HGF-SF," EXS, 65: 41-48 (1993).

*Primary Examiner*—Robert C Hayes
(74) *Attorney, Agent, or Firm*—Ballard Spahr Andrews & Ingersoll, LLP

(57) ABSTRACT

The present invention relates to a novel truncated form of heptocyte growth factor (HGF) which specifically antagonizes the activity of HGF and to a novel truncated form of HGF that is a partial HGF agonist. In particular, the present invention relates to the purification, molecular cloning, recombinant expression of the truncated HGF variants and related pharmaceutical compositions. The present invention further relates to the utilization of the small HGF variants to either inhibit HGF mitogenesis or stimulate HGF mitogenesis in cells expressing the receptor for HGF.

9 Claims, 20 Drawing Sheets

NK2 Coding Sequence

```
                                         27                                              54
ATG TGG GTG ACC AAA CTC CTG CCA GCC CTG CTG CTG CAG CAT GTC CTC CTG CAT
MET Trp Val Thr Lys Leu Leu Pro Ala Leu Leu Leu Gln His Val Leu Leu His 81                                             108
CTC CTC CTG CTC CCC ATC GCC ATC CCC TAT GCA GAG GGA CAA AGG AAA AGA AGA
Leu Leu Leu Leu Pro Ile Ala Ile Pro Tyr Ala Glu Gly Gln Arg Lys Arg Arg 135                                             162
AAT ACA ATT CAT GAA TTC AAA AAA TCA GCA AAG ACT ACC CTA ATC AAA ATA GAT
Asn Thr Ile His Glu Phe Lys Lys Ser Ala Lys Thr Thr Leu Ile Lys Ile Asp 189                                             216
CCA GCA CTG AAG ATA AAA ACC AAA AAA GTG AAT ACT GCA GAC CAA TGT GCT AAT
Pro Ala Leu Lys Ile Lys Thr Lys Lys Val Asn Thr Ala Asp Gln Cys Ala Asn 243                                             270
AGA TGT ACT AGG AAT AAA GGA CTT CCA TTC ACT TGC AAG GCT TTT GTT TTT GAT
Arg Cys Thr Arg Asn Lys Gly Leu Pro Phe Thr Cys Lys Ala Phe Val Phe Asp 297                                             324
AAA GCA AGA AAA CAA TGC CTC TGG TTC CCC TTC AAT AGC ATG TCA AGT GGA GTG
Lys Ala Arg Lys Gln Cys Leu Trp Phe Pro Phe Asn Ser MET Ser Ser Gly Val 351                                             378
AAA AAA GAA TTT GGC CAT GAA TTT GAC CTC TAT GAA AAC AAA GAC TAC ATT AGA
Lys Lys Glu Phe Gly His Glu Phe Asp Leu Tyr Glu Asn Lys Asp Tyr Ile Arg 405                                             432
AAC TGC ATC ATT GGT AAA GGA CGC AGC TAC AAG GGA ACA GTA TCT ATC ACT AAG
Asn Cys Ile Ile Gly Lys Gly Arg Ser Tyr Lys Gly Thr Val Ser Ile Thr Lys 459                                             486
AGT GGC ATC AAA TGT CAG CCC TGG AGT TCC ATG ATA CCA CAC GAA CAC AGC TTT
Ser Gly Ile Lys Cys Gln Pro Trp Ser Ser MET Ile Pro His Glu His Ser Phe 513                                             540
TTG CCT TCG AGC TAT CGG GGT AAA GAC CTA CAG GAA AAC TAC TGT CGA AAT CCT
Leu Pro Ser Ser Tyr Arg Gly Lys Asp Leu Gln Glu Asn Tyr Cys Arg Asn Pro 567                                             594
CGA GGG GAA GAA GGG GGA CCC TGG TGT TTC ACA AGC AAT CCA GAG GTA CGC TAC
Arg Gly Glu Glu Gly Gly Pro Trp Cys Phe Thr Ser Asn Pro Glu Val Arg Tyr 621                                             648
GAA GTC TGT GAC ATT CCT CAG TGT TCA GAA GTT GAA TGC ATG ACC TGC AAT GGG
Glu Val Cys Asp Ile Pro Gln Cys Ser Glu Val Glu Cys MET Thr Cys Asn Gly
```

FIG. 3

```
                                           675                                                      702
GAG AGT TAT CGA GGT CTC ATG GAT CAT ACA GAA TCA GGC AAG ATT TGT CAG CGC
Glu Ser Tyr Arg Gly Leu MET Asp His Thr Glu Ser Gly Lys Ile Cys Gln Arg 729                                                      756
TGG GAT CAT CAG ACA CCA CAC CGG CAC AAA TTC TTG CCT GAA AGA TAT CCC GAC
Trp Asp His Gln Thr Pro His Arg His Lys Phe Leu Pro Glu Arg Tyr Pro Asp 783                                                 810
AAG GGC TTT GAT GAT AAT TAT TGC CGC AAT CCC GAT GGC CAG CCG AGG CCA TGG
Lys Gly Phe Asp Asp Asn Tyr Cys Arg Asn Pro Asp Gly Gln Pro Arg Pro Trp 837                                            864
TGC TAT ACT CTT GAC CCT CAC ACC CGC TGG GAG TAC TGT GCA ATT AAA ACA TGC
Cys Tyr Thr Leu Asp Pro His Thr Arg Trp Glu Tyr Cys Ala Ile Lys Thr Cys

GAG ACA TAA
Glu Thr
```

FIG.3(CONT.)

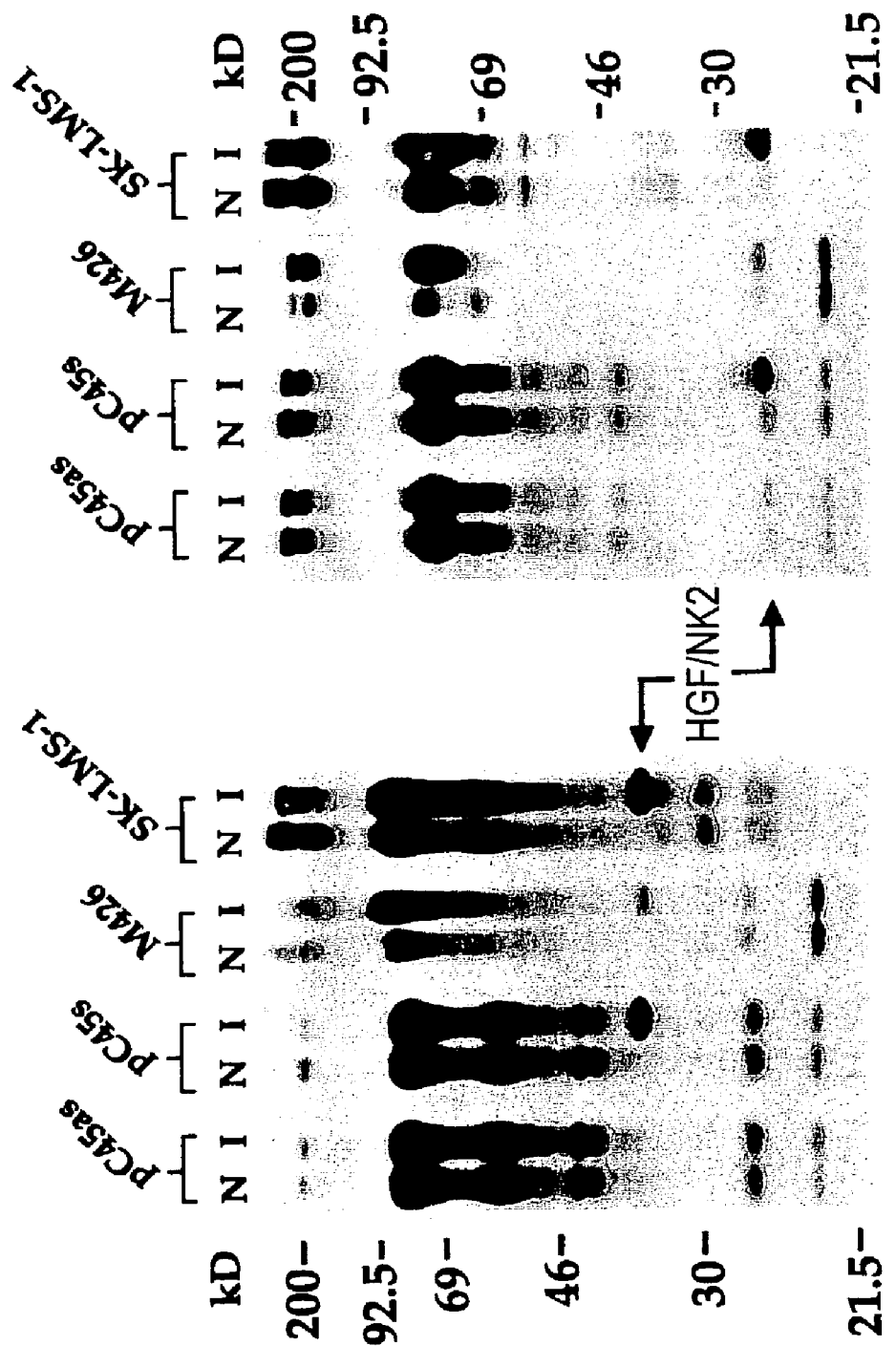
FIG. 5B Non-reducing
FIG. 5A Reducing

NK1 Coding Sequence

```
                                  27                                                        54
ATG TGG GTG ACC AAA CTC CTG CCA GCC CTG CTG CTG CAG CAT GTC CTC CTG CAT
MET Trp Val Thr Lys Leu Leu Pro Ala Leu Leu Leu Gln His Val Leu Leu His 81                                                       108
CTC CTC CTG CTC CCC ATC GCC ATC CCC TAT GCA GAG GGA CAA AGG AAA AGA AGA
Leu Leu Leu Leu Pro Ile Ala Ile Pro Tyr Ala Glu Gly Gln Arg Lys Arg Arg 135                                                       162
AAT ACA ATT CAT GAA TTC AAA AAA TCA GCA AAG ACT ACC CTA ATC AAA ATA GAT
Asn Thr Ile His Glu Phe Lys Lys Ser Ala Lys Thr Thr Leu Ile Lys Ile Asp 189                                                       216
CCA GCA CTG AAG ATA AAA ACC AAA AAA GTG AAT ACT GCA GAC CAA TGT GCT AAT
Pro Ala Leu Lys Ile Lys Thr Lys Lys Val Asn Thr Ala Asp Gln Cys Ala Asn 243                                                       270
AGA TGT ACT AGG AAT AAA GGA CTT CCA TTC ACT TGC AAG GCT TTT GTT TTT GAT
Arg Cys Thr Arg Asn Lys Gly Leu Pro Phe Thr Cys Lys Ala Phe Val Phe Asp 297                                                       324
AAA GCA AGA AAA CAA TGC CTC TGG TTC CCC TTC AAT AGC ATG TCA AGT GGA GTG
Lys Ala Arg Lys Gln Cys Leu Trp Phe Pro Phe Asn Ser MET Ser Ser Gly Val 351                                                       378
AAA AAA GAA TTT GGC CAT GAA TTT GAC CTC TAT GAA AAC AAA GAC TAC ATT AGA
Lys Lys Glu Phe Gly His Glu Phe Asp Leu Tyr Glu Asn Lys Asp Tyr Ile Arg 405                                                       432
AAC TGC ATC ATT GGT AAA GGA CGC AGC TAC AAG GGA ACA GTA TCT ATC ACT AAG
Asn Cys Ile Ile Gly Lys Gly Arg Ser Tyr Lys Gly Thr Val Ser Ile Thr Lys 459                                                       486
AGT GGC ATC AAA TGT CAG CCC TGG AGT TCC ATG ATA CCA CAC GAA CAC AGC TTT
Ser Gly Ile Lys Cys Gln Pro Trp Ser Ser MET Ile Pro His Glu His Ser Phe 513                                                       540
TTG CCT TCG AGC TAT CGG GGT AAA GAC CTA CAG GAA AAC TAC TGT CGA AAT CCT
Leu Pro Ser Ser Tyr Arg Gly Lys Asp Leu Gln Glu Asn Tyr Cys Arg Asn Pro 567                                                       594
CGA GGG GAA GAA GGG GGA CCC TGG TGT TTC ACA AGC AAT CCA GAG GTA CGC TAC
Arg Gly Glu Glu Gly Gly Pro Trp Cys Phe Thr Ser Asn Pro Glu Val Arg Tyr
```

FIG.9

HGF/NK1: Terminal Portion of Coding Sequence and Part of the 3'-Untranslated Sequence of 2.2Kb cDNA Insert

```
GAA GTC TGT GAC ATT CCT CAG TGT TCA GAA GGT AAA TAA ACC TGA ATG CCA TGT
Gln Val Cys Asp Ile Pro Gln Cys Ser Glu Gly Lys                          648
                                    621                          
                                    675

GGG CCA TTC TAT TCC CCC TAT GTG TAG AAC TCA CAT TAA AGG TTA ACA          702
                                    729                                  756
GCA ACG AAT CAA TCA TTT TAT CAA ATA TGT AAA TGC AAC TAC AAA TAA          810
                                    783                                  
TTA TTT AAA CAT TTT TAT ACA ATT TTT TTG GAT TAT CAC CAG ATT              864
                                    837                                  
AAT GCA AAA TAA CAG AGC GAG AAG GTT TGA ATT TCA ACA CTG GAG ACA          918
                                    891                                  
TCC CTC TGG GGA AAG TGA AGA AGA TGT TTT ACT CTA CTG TCT TGA CAC          972
                                    945                                  
ATA CCT CAA AAT CTA CTG CTG TCT GGC ACC TGA AAT GAG CTG AAT GCT TAG      1026
                                    999                                  
CCT TTC ATT AGC AAT GTT AAT TCT ATC TAT CC- CTT --- CCA CAG AAA TTC      1080
                                    1053                                  
TGT CCA AAC TAT CAT GAA GTG TGA CAA TAT AT- GAC --- CCA GAA GAT AAT
                                    1107                                  
AC- ATA T-A GAA GGG ATC ACT GGA AGC CC- --- TTT TGG TGA AAA
TGT GCC TAG AAT CAA ATG TGA CAC AAC TGA GTA CCA TTC AGA ATA
GGA TCT GAA GAG ATC AAA GCA ATG GAG ACC AAA CTG TCT TGA AGG CAT GTC
TAT GGA CCT T
```

FIG.10

DOSE RESPONSE OF B5/589 CELLS TO VARIOUS CONCENTRATIONS OF HGF/SF, HGF/NK$_1$, AND HGF/NK$_2$ IN THE PRESENCE OF INSULIN.

| VARIABLE | AVG CPM (MEAN) | STANDARD ERROR MEASURE (+/−) |
|---|---|---|
| HGF (ng/ml) WITH I | | |
| 100 | 31,696 | 3678 |
| 30 | 28,174 | 1372 |
| 10 | 20,098 | 1697 |
| 3 | 13,501 | 140 |
| 1 | 9634 | 364 |
| 0.3 | 7959 | 407 |
| 0.1 | 7930 | 502 |
| HGF/NK$_1$ WITH I | | |
| 1000 | 23,876 | 1174 |
| 100 | 26,902 | 684 |
| 10 | 18,298 | 257 |
| 1 | 8476 | 700 |
| HGF/NK$_2$ WITH I | | |
| 1000 | 7192 | 157 |
| 100 | 7575 | 469 |
| 10 | 7988 | 1323 |
| 1 | 6915 | 869 |
| 0.1 | 6580 | 568 |
| I | 8944 | 313 |
| E | 25,404 | 1476 |
| I WITH E | 38,525 | 279 |
| BLANK (n=6) | 4047 | 227 |

I=INSULIN AT 5ng/ml
E=EPIDERMAL GROWTH FACTOR AT 5ng/ml

FIG.15

SEQUENCE LISTING

<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Artificial Sequence:/ Note = synthetic
      construct

<400> SEQUENCE: 1
agtactgtgc aattaaaaca tgcg                                              24

<210> SEQ ID NO 2
<211> LENGTH: 27
<212> TYPE: DNA
<213> ORGANISM: Artificial Sequence
<220> FEATURE:
<223> OTHER INFORMATION: Artificial Sequence:/ Note = synthetic
      construct

<400> SEQUENCE: 2
gtagaaaaat gattgtatgg actgcta                                           27

<210> SEQ ID NO 3
<211> LENGTH: 32
<212> TYPE: DNA
<213> ORGANISM: Artificial Sequence
<220> FEATURE:
<223> OTHER INFORMATION: Artificial Sequence:/ Note = synthetic
      construct

<400> SEQUENCE: 3
atggatccag tactgtgcaa ttaaaacatg cg                                     32

<210> SEQ ID NO 4
<211> LENGTH: 34
<212> TYPE: DNA
<213> ORGANISM: Artificial Sequence
<220> FEATURE:
<223> OTHER INFORMATION: Artificial Sequence:/ Note = synthetic
      construct

<400> SEQUENCE: 4
atggatccta gaaaatgat tgtatggact gcta                                    34

<210> SEQ ID NO 5
<211> LENGTH: 45
<212> TYPE: DNA
<213> ORGANISM: Artificial Sequence
<220> FEATURE:
<223> OTHER INFORMATION: Artificial Sequence:/ Note = synthetic
      construct

<400> SEQUENCE: 5
aggcactgac tccgaacagg attctttcac ccaggcatct cctcc                       45

<210> SEQ ID NO 6
<211> LENGTH: 34
<212> TYPE: DNA
<213> ORGANISM: Artificial Sequence
<220> FEATURE:
<223> OTHER INFORMATION: Artificial Sequence:/ Note = synthetic
      construct

<400> SEQUENCE: 6

```
atggatcctt atgtctcgca tgttttaatg caca                               34
```

<210> SEQ ID NO 7
<211> LENGTH: 873
<212> TYPE: DNA
<213> ORGANISM: Artificial Sequence
<220> FEATURE:
<223> OTHER INFORMATION: Artificial Sequence:/ Note = synthetic
      construct
<220> FEATURE:
<221> NAME/KEY: CDS
<222> LOCATION: (1)...(873)

<400> SEQUENCE: 7

```
atg tgg gtg acc aaa ctc ctg cca gcc ctg ctg ctg cag cat gtc ctc    48
Met Trp Val Thr Lys Leu Leu Pro Ala Leu Leu Leu Gln His Val Leu
 1               5                  10                  15 ctg cat ctc ctc ctg ctc ccc atc gcc atc ccc tat gca gag gga caa    96
Leu His Leu Leu Leu Leu Pro Ile Ala Ile Pro Tyr Ala Glu Gly Gln
             20                  25                  30 agg aaa aga aga aat aca att cat gaa ttc aaa aaa tca gca aag act   144
Arg Lys Arg Arg Asn Thr Ile His Glu Phe Lys Lys Ser Ala Lys Thr
         35                  40                  45 acc cta atc aaa ata gat cca gca ctg aag ata aaa acc aaa aaa gtg   192
Thr Leu Ile Lys Ile Asp Pro Ala Leu Lys Ile Lys Thr Lys Lys Val
     50                  55                  60 aat act gca gac caa tgt gct aat aga tgt act agg aat aaa gga ctt   240
Asn Thr Ala Asp Gln Cys Ala Asn Arg Cys Thr Arg Asn Lys Gly Leu
 65                  70                  75                  80 cca ttc act tgc aag gct ttt gtt ttt gat aaa gca aga aaa caa tgc   288
Pro Phe Thr Cys Lys Ala Phe Val Phe Asp Lys Ala Arg Lys Gln Cys
                 85                  90                  95 ctc tgg ttc ccc ttc aat agc atg tca agt gga gtg aaa aaa gaa ttt   336
Leu Trp Phe Pro Phe Asn Ser Met Ser Ser Gly Val Lys Lys Glu Phe
            100                 105                 110 ggc cat gaa ttt gac ctc tat gaa aac aaa gac tac att aga aac tgc   384
Gly His Glu Phe Asp Leu Tyr Glu Asn Lys Asp Tyr Ile Arg Asn Cys
        115                 120                 125 atc att ggt aaa gga cgc agc tac aag gga aca gta tct atc act aag   432
Ile Ile Gly Lys Gly Arg Ser Tyr Lys Gly Thr Val Ser Ile Thr Lys
    130                 135                 140 agt ggc atc aaa tgt cag ccc tgg agt tcc atg ata cca cac gaa cac   480
Ser Gly Ile Lys Cys Gln Pro Trp Ser Ser Met Ile Pro His Glu His
145                 150                 155                 160 agc ttt ttg cct tcg agc tat cgg ggt aaa gac cta cag gaa aac tac   528
Ser Phe Leu Pro Ser Ser Tyr Arg Gly Lys Asp Leu Gln Glu Asn Tyr
                165                 170                 175 tgt cga aat cct cga ggg gaa gaa ggg gga ccc tgg tgt ttc aca agc   576
Cys Arg Asn Pro Arg Gly Glu Glu Gly Gly Pro Trp Cys Phe Thr Ser
            180                 185                 190 aat cca gag gta cgc tac gaa gtc tgt gac att cct cag tgt tca gaa   624
Asn Pro Glu Val Arg Tyr Glu Val Cys Asp Ile Pro Gln Cys Ser Glu
        195                 200                 205 gtt gaa tgc atg acc tgc aat ggg gag agt tat cga ggt ctc atg gat   672
Val Glu Cys Met Thr Cys Asn Gly Glu Ser Tyr Arg Gly Leu Met Asp
    210                 215                 220 cat aca gaa tca ggc aag att tgt cag cgc tgg gat cat cag aca cca   720
His Thr Glu Ser Gly Lys Ile Cys Gln Arg Trp Asp His Gln Thr Pro
225                 230                 235                 240 cac cgg cac aaa ttc ttg cct gaa aga tat ccc gac aag ggc ttt gat   768
His Arg His Lys Phe Leu Pro Glu Arg Tyr Pro Asp Lys Gly Phe Asp
```

```
                  245                 250                 255
gat aat tat tgc cgc aat ccc gat ggc cag ccg agg cca tgg tgc tat      816
Asp Asn Tyr Cys Arg Asn Pro Asp Gly Gln Pro Arg Pro Trp Cys Tyr
            260                 265                 270 act ctt gac cct cac acc cgc tgg gag tac tgt gca att aaa aca tgc      864
Thr Leu Asp Pro His Thr Arg Trp Glu Tyr Cys Ala Ile Lys Thr Cys
        275                 280                 285 gag aca taa                                                          873
Glu Thr *
    290

<210> SEQ ID NO 8
<211> LENGTH: 290
<212> TYPE: PRT
<213> ORGANISM: Artificial Sequence
<220> FEATURE:
<223> OTHER INFORMATION: Artificial Sequence :/ Note = synthetic
      construct

<400> SEQUENCE: 8

Met Trp Val Thr Lys Leu Leu Pro Ala Leu Leu Leu Gln His Val Leu
 1               5                  10                  15

Leu His Leu Leu Leu Leu Pro Ile Ala Ile Pro Tyr Ala Glu Gly Gln
             20                  25                  30

Arg Lys Arg Arg Asn Thr Ile His Glu Phe Lys Lys Ser Ala Lys Thr
         35                  40                  45

Thr Leu Ile Lys Ile Asp Pro Ala Leu Lys Ile Lys Thr Lys Lys Val
     50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285
```

```
Glu Thr
    290

<210> SEQ ID NO 9
<211> LENGTH: 648
<212> TYPE: DNA
<213> ORGANISM: Artificial Sequence
<220> FEATURE:
<223> OTHER INFORMATION: Artificial Sequence:/ Note = synthetic
      construct
<220> FEATURE:
<221> NAME/KEY: CDS
<222> LOCATION: (1)...(649)

<400> SEQUENCE: 9 atg tgg gtg acc aaa ctc ctg cca gcc ctg ctg ctg cag cat gtc ctc      48
Met Trp Val Thr Lys Leu Leu Pro Ala Leu Leu Leu Gln His Val Leu
 1               5                  10                  15 ctg cat ctc ctc ctg ctc ccc atc gcc atc ccc tat gca gag gga caa      96
Leu His Leu Leu Leu Leu Pro Ile Ala Ile Pro Tyr Ala Glu Gly Gln
             20                  25                  30 agg aaa aga aga aat aca att cat gaa ttc aaa aaa tca gca aag act     144
Arg Lys Arg Arg Asn Thr Ile His Glu Phe Lys Lys Ser Ala Lys Thr
         35                  40                  45 acc cta atc aaa ata gat cca gca ctg aag ata aaa acc aaa aaa gtg     192
Thr Leu Ile Lys Ile Asp Pro Ala Leu Lys Ile Lys Thr Lys Lys Val
     50                  55                  60 aat act gca gac caa tgt gct aat aga tgt act agg aat aaa gca ctt     240
Asn Thr Ala Asp Gln Cys Ala Asn Arg Cys Thr Arg Asn Lys Ala Leu
 65                  70                  75                  80 cca ttc act tgc aag gct ttt gtt ttt gat aaa gca aga aaa caa tgc     288
Pro Phe Thr Cys Lys Ala Phe Val Phe Asp Lys Ala Arg Lys Gln Cys
                 85                  90                  95 ctc tgg ttc ccc ttc aat agc atg tca agt gga gtg aaa aaa gaa ttt     336
Leu Trp Phe Pro Phe Asn Ser Met Ser Ser Gly Val Lys Lys Glu Phe
            100                 105                 110 ggc cat gaa ttt gac ctc tat gaa aac aaa gac tac att aga aac tgc     384
Gly His Glu Phe Asp Leu Tyr Glu Asn Lys Asp Tyr Ile Arg Asn Cys
        115                 120                 125 atc att ggt aaa gga cgc agc tac aag gga aca gta tct atc act aag     432
Ile Ile Gly Lys Gly Arg Ser Tyr Lys Gly Thr Val Ser Ile Thr Lys
    130                 135                 140 agt ggc atc aaa tgt cag ccc tgg agt tcc atg ata cca cac gaa cac     480
Ser Gly Ile Lys Cys Gln Pro Trp Ser Ser Met Ile Pro His Glu His
145                 150                 155                 160 agc ttt ttg cct tcg agc tat cgg ggt aaa gac cta cag gaa aac tac     528
Ser Phe Leu Pro Ser Ser Tyr Arg Gly Lys Asp Leu Gln Glu Asn Tyr
                165                 170                 175 tgt cga aat cct cga ggg gaa gaa ggg gga ccc tgg tgt ttc aca agc     576
Cys Arg Asn Pro Arg Gly Glu Glu Gly Gly Pro Trp Cys Phe Thr Ser
            180                 185                 190 aat cca gag gta cgc tac gaa gtc tgt gac att cct cag tgt tca gaa     624
Asn Pro Glu Val Arg Tyr Glu Val Cys Asp Ile Pro Gln Cys Ser Glu
        195                 200                 205 gaa att ctg tcc aaa cta tca tga                                     648
Glu Ile Leu Ser Lys Leu Ser  *
    210                 215

<210> SEQ ID NO 10
<211> LENGTH: 215
<212> TYPE: PRT
<213> ORGANISM: Artificial Sequence
<220> FEATURE:
```

<223> OTHER INFORMATION: Artificial Sequence:/ Note = synthetic
     construct

<400> SEQUENCE: 10

Met Trp Val Thr Lys Leu Leu Pro Ala Leu Leu Leu Gln His Val Leu
 1               5                  10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Ala Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Glu Ile Leu Ser Lys Leu Ser
    210                 215

<210> SEQ ID NO 11
<211> LENGTH: 658
<212> TYPE: DNA
<213> ORGANISM: Artificial Sequence
<220> FEATURE:
<223> OTHER INFORMATION: Artificial Sequence:/ Note = synthetic
     construct
<220> FEATURE:
<221> NAME/KEY: misc_feature
<222> LOCATION: (1)...(658)
<223> OTHER INFORMATION: Note: n = a, g, c or t(u)

<400> SEQUENCE: 11
gaagtctgtg acaatcctca gtgttcagaa ggtaaataaa cctgaatgcc atgtgggcca      60
ttctattccc cctatgtgta gaactgtaac tcacattaaa ggttaacagc aacgaatcaa     120
tcataacaaa tatgttgttc gtgcaaatgc aactacaaat aattatttaa acatttttat     180 acaattttt taaaactgtt ggattatcac cagattaatg caaaataaca gagcgagtta     240
tcagtttgaa tttcaacact gcctgagaca tccctctggg gaaagtgaaa gagagggttt     300
acttacctac tgtcttgagc tcacatacct caaaatctac tactgtgtgg cacctgaaag     360
gagttgaatg aagcttagcc tttcattagc aatgttaatt ctatcaacca gcacctgctt     420
ccacagaaat tctgtccaaa ctatcatgaa gtggtgtgac aagggtatat ngacccagaa     480
gataatacna tatnaggaag gatcactgga agcttgaccc cnnnnnnntt ttggtgaaaa     540

```
                                  -continued tgtgcctaga atcaaatgtg acacgtaggc tggaactgag taccattcag aataggatct      600
gaagagatca aagcaatgga gaccaccaaa ctgtcttgaa ggcatgtcta tggacctt       658

<210> SEQ ID NO 12
<211> LENGTH: 12
<212> TYPE: PRT
<213> ORGANISM: Artificial Sequence
<220> FEATURE:
<223> OTHER INFORMATION: Artificial Sequence:/ Note = synthetic
      construct

<400> SEQUENCE: 12

Glu Val Cys Asp Ile Pro Glu Cys Ser Glu Gly Lys
 1               5                  10

<210> SEQ ID NO 13
<211> LENGTH: 416
<212> TYPE: DNA
<213> ORGANISM: Artificial Sequence
<220> FEATURE:
<223> OTHER INFORMATION: Artificial Sequence:/ Note = synthetic
      construct
<220> FEATURE:
<221> NAME/KEY: misc_feature
<222> LOCATION: 1-416
<223> OTHER INFORMATION: Note: n = a, g, c or t(u)

<400> SEQUENCE: 13
gtaagtgann nnnnnnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnct ccccag          416
```

TRUNCATED HEPATOCYTE GROWTH FACTOR VARIANT PROTEIN HGF/NK2

This is a divisional application of application Ser. No. 08/484,841 filed on Jun. 7, 1995, now U.S. Pat. No. 6,566,098 which is a continuation-in-part of application Ser. No. 08/130,134 filed on Oct. 4, 1993 (now abandoned), which is a continuation-in-part of application Ser. No. 07/655,502 filed on Feb. 15, 1991 (now abandoned), which is a continuation-in-part of application Ser. No. 07/582,063 filed on Sep. 14, 1990 (now abandoned), all of which are incorporated herein, in their entireties, by this reference.

BACKGROUND OF THE INVENTION

1. Field of the Invention

The present invention relates to naturally occurring truncated forms of Hepatocyte Growth Factor (HGF), which are encoded by alternative HGF mRNA transcripts. In particular, the present invention relates to a small HGF variant, HGF/NK2, which is a competitive antagonist of HGF, and HGF/NK1, which is a partial agonist of HGF.

2. Background Information

Hepatocyte growth factor has hormone-like activity and is released in response to partial hepatectomy and liver injury and is presumed to be an important mediator of liver regeneration (Nakamura et al., *FEBS Lett.* 224: 311 (1987); Gohda et al., *J. Clin. Invest.* 81: 414-419 (1988); R. Zarnegar and G. Michaelopoulous, *Cancer Research* 49: 3314-3320 (1989)). Its ubiquitous expression by stromal fibroblasts and demonstrated ability to stimulate DNA synthesis in melanocytes and endothelial cells as well as epithelial cells suggest that this factor plays a role in paracrine regulation of cell growth as well (Rubin et al., *Proc. Natl. Acad. Sci. USA* 88: 415 (1991)). Reports showing that scatter factor has high amino acid sequence identity to HGF over restricted regions, suggested that HGF may also be involved in modulating cell-cell interactions and migration (E. Gherardi and M. Stoker, *Nature* 346: 288 (1990); Weidner et al., *J. Cell Biology* 111: 2097-2108 (1990)). This has been borne out by subsequent studies that verify the identity of scatter factor and HGF.

Structurally, HGF resembles plasminogen in that it possesses characteristic kringle domains (Patthy et al., *FEBS Lett.* 171: 131-136 (1984)) and a serine protease-like domain (Miyazawa et al., *Biochem. Biophys. Res. Commun.*, 163: 967-973 (1989); Nakamura et al., *Nature* 342: 440-443 (1989)). Like plasminogen, HGF can be processed by proteolytic cleavage, generating a heterodimeric molecule comprised of a heavy- and light-chain covalently linked by disulfide bonds (Nakamura et al., *Nature* 342: 440-443 (1989) and Miyazawa et al., *Biochem. Biophys. Res. Commun.* 163: 967-973 (1989)) The possibility that its actions might be mediated by a receptor tyrosine kinase was suggested by its rapid stimulation of tyrosine phosphorylation of cellular proteins in target cells (Rubin et al., *Proc. Natl. Acad. Sci. U.S.A.* 88: 415 (1991)). Recent studies have directly identified the HGF receptor as the c-met protooncogene product (Bottaro et al., *Science* 251: 802 (1991)), whose structure resembles that of a membrane-spanning tyrosine kinase (Park et al., *Proc. Natl. Acad. Sci. USA* 84: 6379-6383 (1987); Chan et al., *Oncogene* 2: 593-599 (1988)).

There is accumulating evidence that the positive effects of growth factors on cell proliferation can be counteracted at a variety of levels both intracellularly (Moses et al., *Cell* 63: 245-247 (1990) and at the cell surface (Hannum et al., *Science* 343: 336-340 (1990), Eisenberg, et al., *Nature* 343: 341-346 (1990); Carter et al., *Nature* 344: 633-637 (1990)). Thus, the potential exists to find an antagonist to HGF which would negatively regulate the growth factor's proliferation effects. The invention described herein relates to small HGF variants and their corresponding transcripts. Characterization of one of these HGF variants, HGF/NK2, has revealed that it is a competitive antagonist of HGF action and thus establishes a novel regulatory mechanism whereby the same gene encodes both an agonist and antagonist of growth factor action. Characterization of another HGF variant, HGF/NK1, revealed that it is a partial agonist of HGF in vitro.

SUMMARY OF THE INVENTION

Although those of skill in the art of the invention possessed knowledge of HGF, no one knew about or could have predicted the existence of alternative mRNA transcripts encoding the claimed variants. Indeed, the inventors discovered HGF/NK1 and HGF/NK2, none of the work related to HGF even remotely suggested that a small transcript, particularly one, such as HGF/NK2, that is an HGF antagonist, or HGF/NK1, that is a partial HGF agonist, existed.

Thus, in one embodiment, the invention relates to a substantially pure HGF variant that is a truncated form of HGF comprising the N-terminal and first two kringle domains of HGF, and that specifically inhibits HGF-induced mitogenesis.

In another embodiment, the invention relates to a substantially pure HGF variant that is a truncated form of HGF comprising the N-terminal and the first kringle domain of HGF, and that is a partial HGF agonist.

In yet another embodiment, the invention relates to a method of inhibiting HGF induced mitogenesis in cells expressing the receptor for HGF, comprising contacting the cells with a mitogenesis-inhibiting amount of the HGF variant HGF/NK2, such that HGF induced mitogenesis is inhibited when the HGF variant binds the receptor for HGF on the cells.

In another embodiment, the invention relates to a method of stimulating mitogenesis in cells expressing the receptor for HGF, comprising contacting the cells with a mitogenesis-stimulating amount of HGF/NK1, such that mitogenesis is stimulated when the HGF variant binds the receptor for HGF on the cells.

In another embodiment, the invention relates to an isolated and substantially pure DNA molecule that encodes HGF/NK2.

In another embodiment, the invention relates to an isolated and substantially pure DNA molecule that encodes HGF/NK1.

In another embodiment, the invention relates to a recombinant vector comprising the above DNAs.

In another embodiment, the invention relates to a host cell stably or transiently transfected with the above described DNA in a manner allowing expression of the protein encoded by the DNA.

Another embodiment of the invention relates to a method of producing a recombinant HGF variant, comprising culturing the above host cell in a manner allowing expression of a protein and isolating the protein from the host cell.

In another embodiment, the invention relates to a method of producing the above described substantially pure HGF variant protein, the method comprising the following steps:

(i) culturing HGF variant-producing cells in a culture medium under conditions such that HGF variant is produced;

(ii) concentrating the culture medium so that a concentrate is formed;

(iii) contacting the concentrate with heparin under conditions such that HGF variant in the concentrate binds to the heparin, whereby a heparin-HGF variant complex is formed;

(iv) separating the heparin-HGF variant complex from the concentrate;

(v) treating the heparin-HGF variant complex under conditions such that the HGF variant dissociates from the heparin so that a solution of free HGF variant is formed;

(vi) fractionating the solution by sizing chromatography and/or reverse phase HPLC so that HGF variant is separated from the remaining components.

In another embodiment, the invention relates to a method of producing a substantially pure and biologically active Hepatocyte Growth Factor (HGF) variant comprising the steps of:

(i) disrupting HGF variant-producing bacteria that have been cultured in a culture medium under conditions such that HGF variant is expressed, so as to produce a first HGF variant protein-containing suspension;

(ii) recovering the protein from the first suspension and, washing and solubilizing the recovered protein, wherein the solubilizing is performed with a denaturant and reducing agent, and wherein a second protein-containing suspension is produced;

(iii) fractionating the second suspension by sizing chromatography with a solvent containing a denaturant and a reducing agent;

(iv) removing the denaturant from the fractions of step (iii) and pooling selected fractions containing denatured HGF variant;

(v) purifying said HGF variant in the pooled fractions by reverse phase chromatography;

(vi) lyophilizing the purified HGF variant of step (v) and redissolving the lyophilized HGF variant with denaturing and reducing agents;

(vii) serially diluting and then incubating the redissolved lyophilized proteins in refolding buffer, and then removing the denaturant by dialysis, so as to produce a third suspension containing biologically active proteins;

(viii) concentrating and then purifying said dialyzed proteins in the third suspension by sizing chromatography, so as to produce several fractions containing biologically active HGF variant; and (ix) pooling and then concentrating the fractions containing biologically active HGF variant.

In a further embodiment, the present invention relates to therapeutic applications of the above described HGF variant that inhibits mitogenesis. Such applications could be used in proliferative disorders including both cancer and non-malignant conditions, in which HGF is excessive. The method comprises specifically blocking the action of HGF by administering a therapeutic amount of the HGF variant or by inducing the endogenous expression of increased amounts of the inhibitor.

The present invention also relates to therapeutic methods that decrease the overproduction of the HGF variant that inhibits mitogenesis. Such methods are applicable where HGF variant is inappropriately produced at high levels in a setting of impaired cell renewal. The method comprises specifically blocking the synthesis or action of the HGF variant by either contacting inhibitor HGF transcripts with antisense oligonucleotides or contacting inhibitor HGF protein with antibodies specific for the inhibitor molecules.

In yet another embodiment, the present invention relates to ex vivo methods of stimulating the growth of cells expressing the receptor for HGF. After proliferation, such cells can be transplanted into a subject in need of such cells. Such methods involve contacting the cells with growth-stimulating amounts of HGF/NK1 in culture prior to transplantation.

In yet another embodiment, the present invention relates to in vivo and in vitro methods of screening chemotherapeutic agents by using HGF/NK1 or HGF/NK2 as a carrier for chemotherapeutic agents that may be toxic to cells expressing the receptor for HGF. Because both HGF/NK1 and HGF/NK2 bind specifically to the HGF receptors on cells and are not themselves toxic, HGF/NK1 or HGF/NK2 can be used to carry potential toxins to such cells, thereby permitting evaluation of the efficacy of various toxins as chemotherapeutic agents.

In yet another embodiment, the invention relates to pharmaceutical compositions comprising either a mitogenesis-inhibitory amount of the HGF/NK2 or mitogenesis-stimulating amount of HGF/NK1 and a pharmaceutically acceptable carrier.

Various other objects and advantages of the present invention will become obvious from the drawings and the following description of the invention.

BRIEF DESCRIPTION OF THE DRAWINGS

FIG. 3 shows the cDNA coding sequence (SEQ ID NO: 7) and corresponding amino acid sequence (SEQ ID NO: 8) of the 34 kd HGF variant, HGF/NK2.

| P1 | agtactgtgcaattaaaacatgcg | (SEQ ID NO: 1) |
| P2 | gtagaaaatgattgtatggactgcta | (SEQ ID NO: 2) |
| P1(B) | atggatccagtactgtgcaattaaaacatgcg | (SEQ ID NO: 3) |

-continued

P2(B)  atggatcctagaaaaatgattgtatggactgcta   (SEQ ID NO: 4)

P3     aggcactgactccgaacaggattctttcacccaggcatctcctcc   (SEQ ID NO: 5)

P4     atggatccttatgtctcgcatgttttaatgcaca   (SEQ ID NO: 6)

Figure 4A:
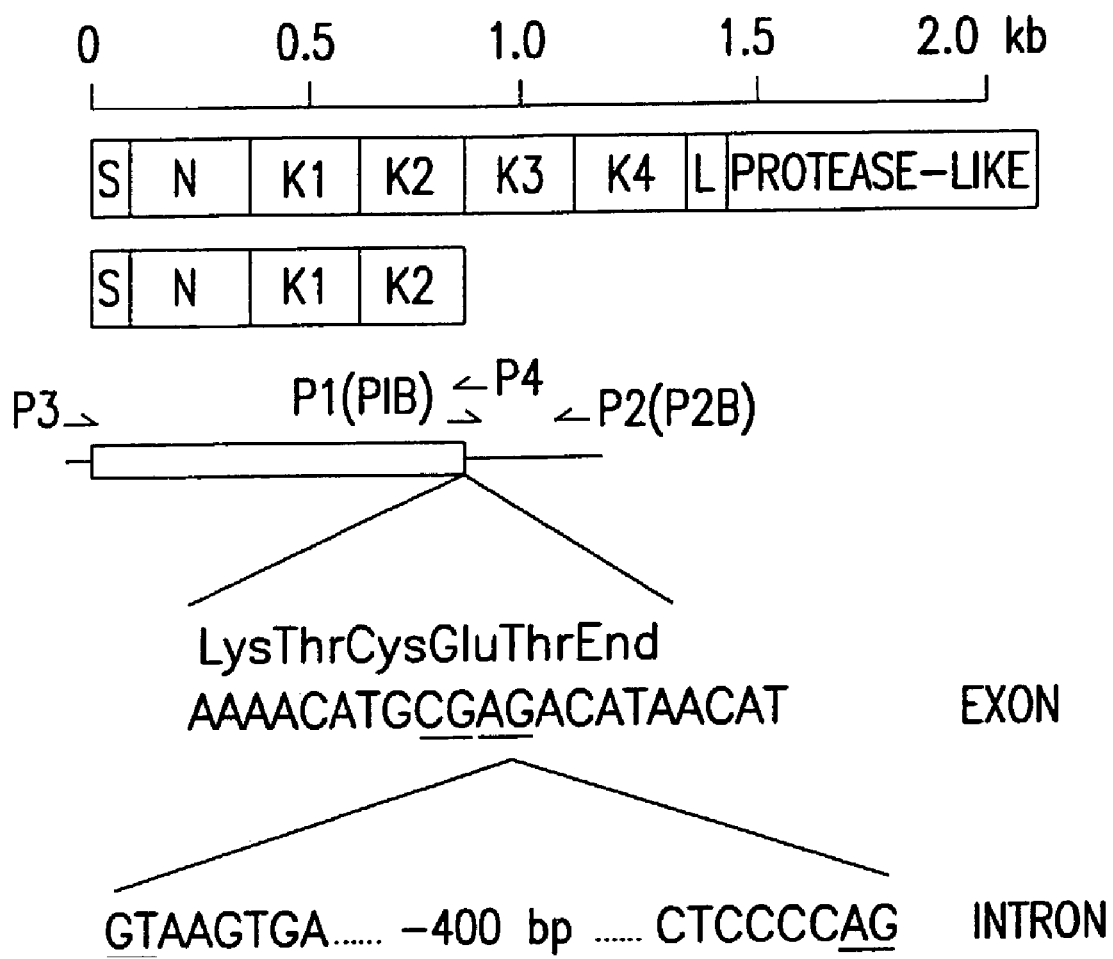
FIG. 4(A) is a schematic representation of the domain structures of HGF and HGF/NK2 (openboxes). The 1.2 kb cDNA clone pH45, comprised of a coding (open bar) and untranslated regions (solid lines). Arrows represent the positions and directions of PCR primers utilized. The cDNA and the predicted amino acid sequences of HGF/NK2 (EXON) (amino acid position #s 286-290 of SEQ ID NO:8) at the point of divergence with HGF are shown with the splice site indicated. The corresponding genomic region (INTRON) includes a –400 bp intron with the consensus splicing signals at the exon-intron boundaries underlined (SEQ ID NO: 13). Abbreviations are: S, signal peptide; N, N-terminal domain; K1-K4, kringle 1 to 4; and L, linker region. Primers are.
Figure 4B:
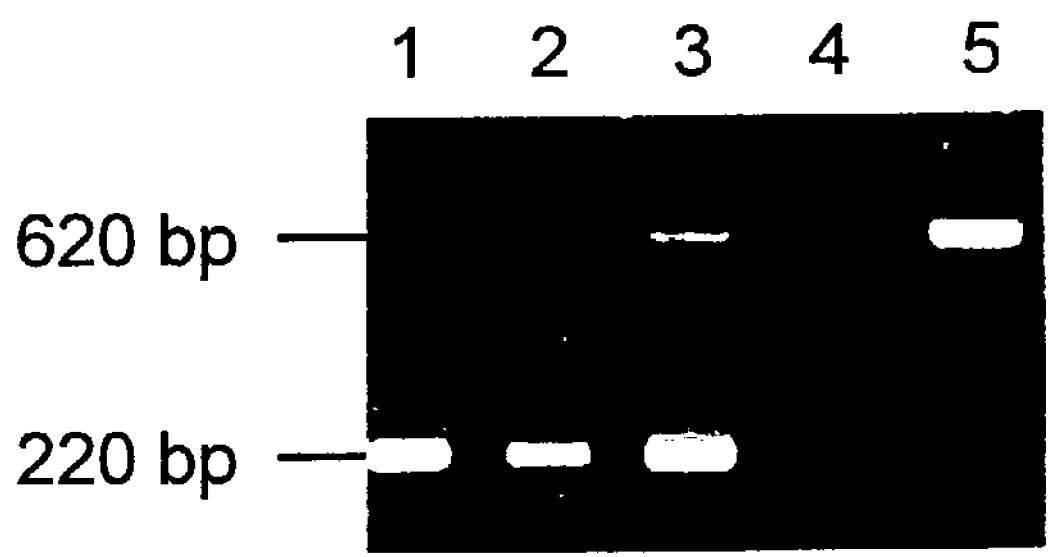
FIG. 4 generally provides further characterization of a HGF/NK2 cDNA (SEQ ID NO: 7).

FIG. 4(B) shows the detection of HGF/NK2 transcript by PCR amplification. Samples included positive control plasmid pH45 (lane 1), RNAs from M426 (lane 2), SK-LMS-1 (lane 3), and B5/589 (lane 4); and genomic DNA from M426 cells (Lane 5). Primers P1 and P2 were used in the amplification reactions and PCR fragments (220 and 620 bp) generated are indicated. The faint 620 bp band in lane 3 is indicative of unprocessed HGF RNA or genomic DNA in the SK-LMS-1 RNA preparation.

FIG. 5 demonstrates the expression of HGF/NK2 cDNA in COS-1 cells. Conditioned medium from COS-1 cells transfected with plasmid pC45as (antisense construct) or pC45s (sense construct) as well as M426 and SK-LMS-1 cells were immunoprecipitated with non-immune (N) or HGF antiserum (I). Samples were analyzed under both reducing (A) and nonreducing (B) conditions. Specific HGF/NK2 immunoreactive species are indicated by arrows.

Figure 6:
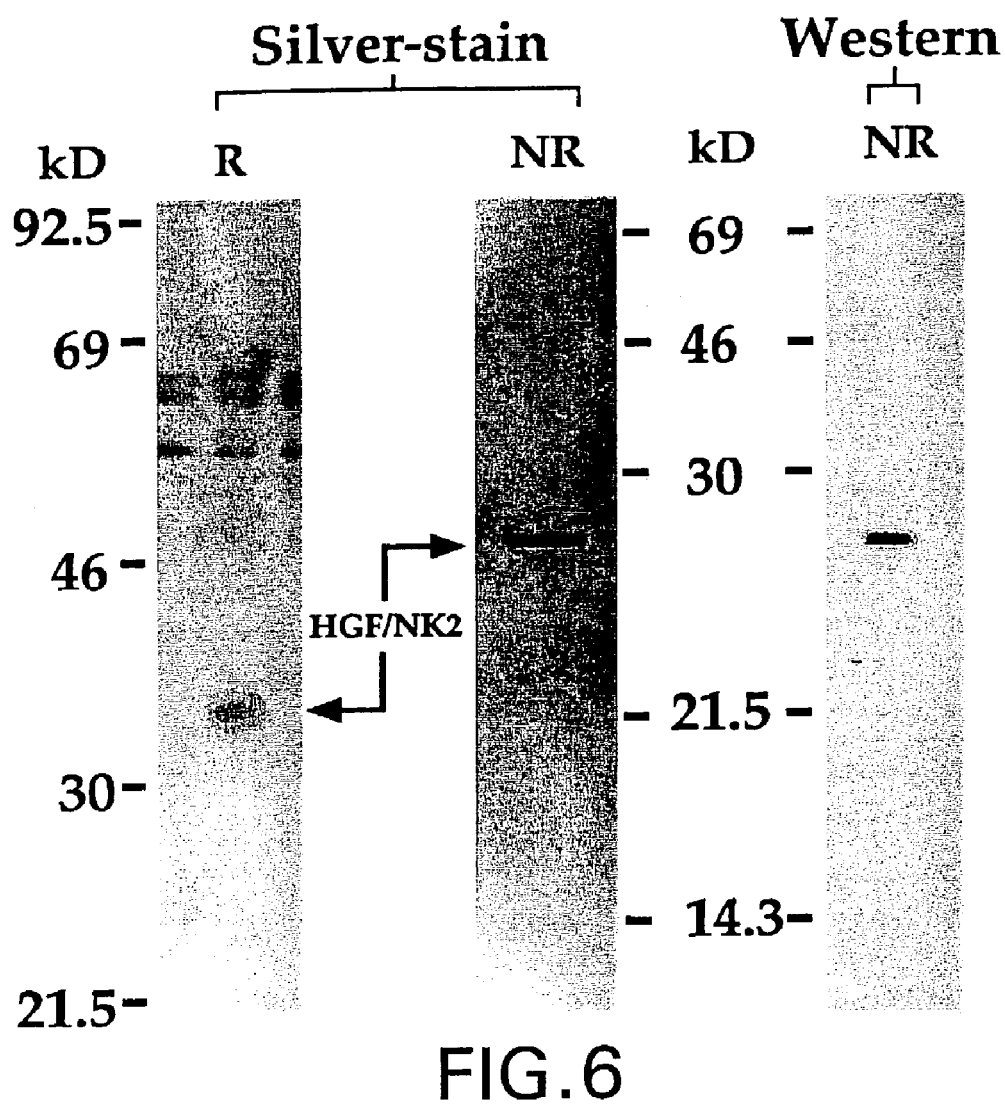

FIG. 6 shows purified naturally occurring HGF/NK2 (SEQ ID NO: 8). HGF/NK2 was purified from conditioned medium of SK-LMS-1 cells as described in the Examples. Aliquots from selected fractions eluted from a TSK sizing column were analyzed on 10% SDS-PAGE under reducing conditions (R) or 14% SDS-PAGE under non-reducing conditions (NR) and detecting by the silver-stain technique. HGF/NK2 was visualized as a single band migrating at 34 and 28 kD, respectively (Arrows). Higher molecular weight artifactual bands were observed under reducing conditions. An identical sample was subjected to 14% SDS-PAGE under non-reducing conditions and immunoblotted with HGF antiserum.

FIG. 7 depicts the analysis of HGF/NK2 biological activity.

Figure 7A:
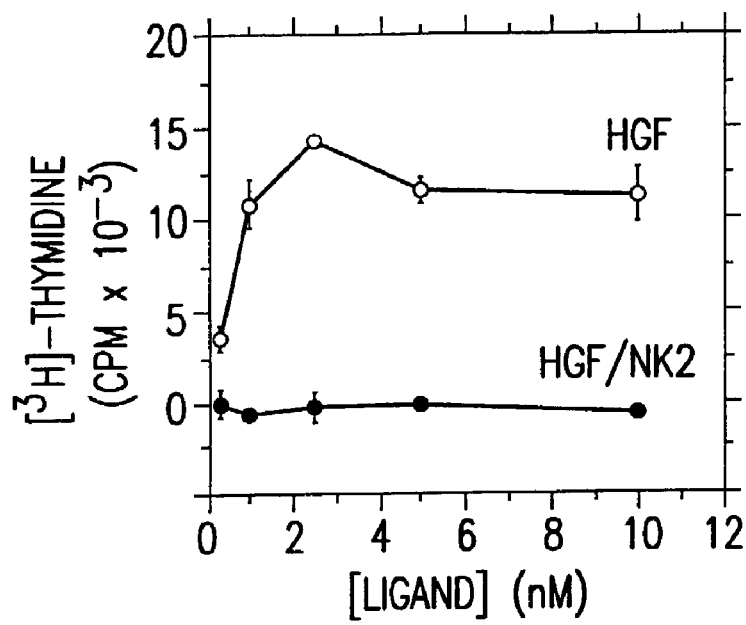

FIG. 7(A) shows a comparison of DNA synthesis stimulated by HGF (-)) and HGF/NK2 (-•-). B5/589 cells were exposed to increasing concentrations of protein, and $[-^3H]$-thymidine incorporation was measured as described in the experimental procedures.

Figure 7B:
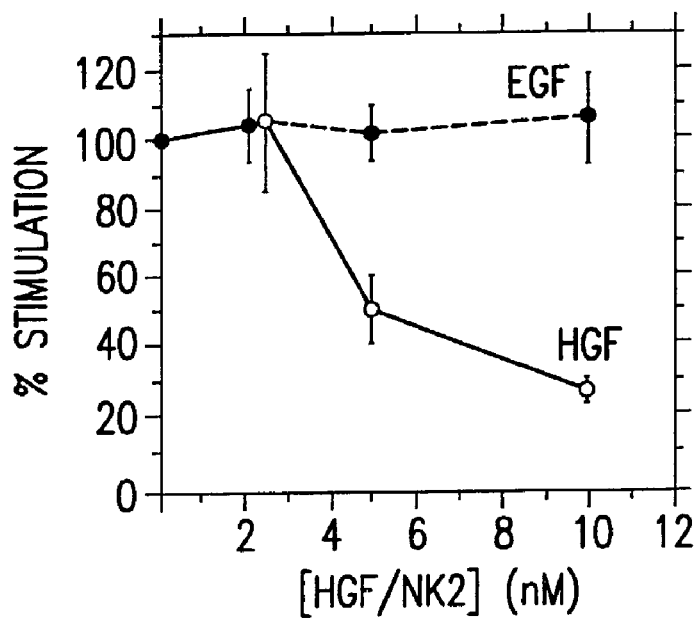

FIG. 7(B) shows the effect of HGF/NK2 on HGF (-o-) and EGF (--•--)-induced $[-^3H]$-thymidine incorporation by B5/589 cells. Results are expressed as the percentage of stimulation in the absence of HGF/NK2. HGF- and EGF-treated cells were tested at growth factor concentrations (0.2 nM and 0.3 nM, respectively) in the linear range of their dose-response curves.

Typically, the stimulation was 10,000-20 cpm with a background of 2000 cpm.

For both 7(A) and 7(B), each data point is the mean ± standard deviation of triplicate measurements; when no error bar is shown, the error was less than the symbol size.

Figure 8:
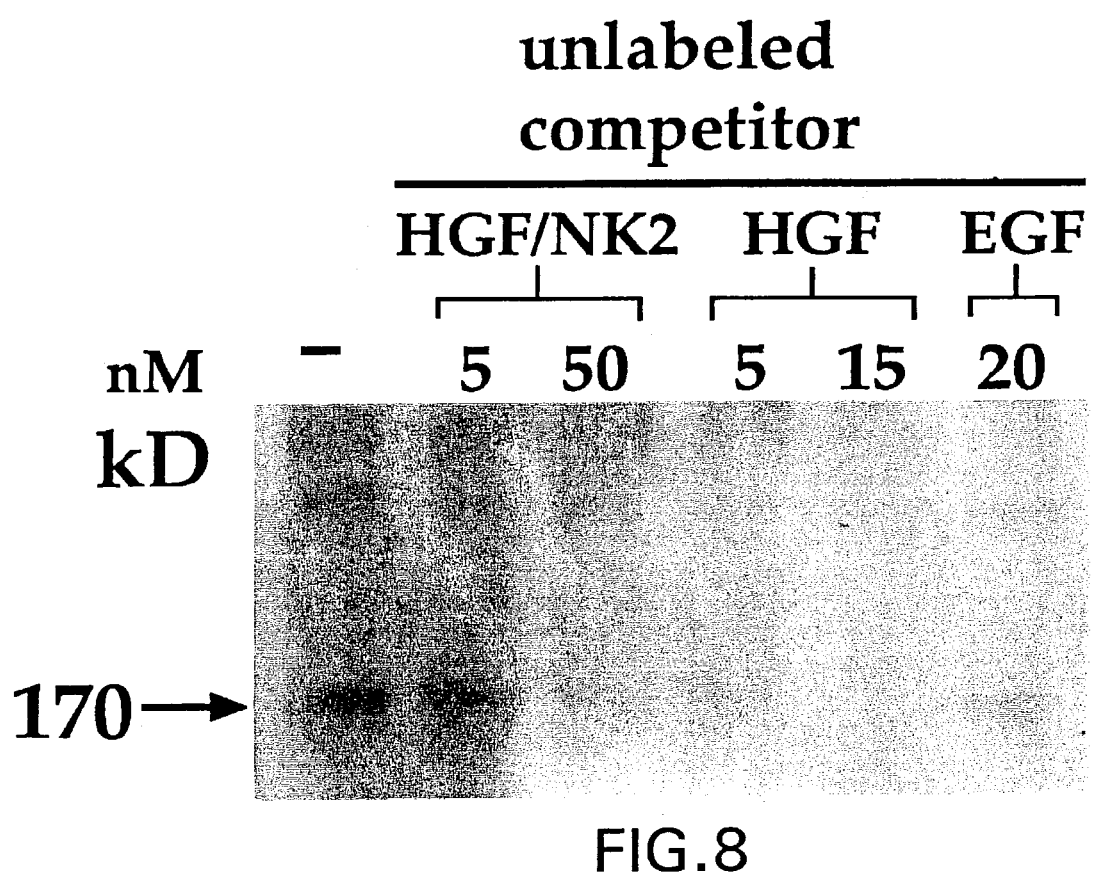

FIG. 8 shows the cross-linking and competition analysis of HGF/NK2 to the HGF receptor. $[^{125}I]$-HGF/NK2 was incubated with B5/589 cells in the presence or absence of HGF/NK2, HGF, or EGF at the concentrations indicated for 45 minutes at 22° C. Cultures were then washed with HEPES saline and incubated for 15 minutes with the cross-linking agent, disuccinimidyl suberate. Total cell lysates were resolved by 6.5% SDS-PAGE under reducing conditions and the dried gel was exposed to X-ray film at −70° C. for 32 days.

FIG. 9 show the cDNA coding sequence, as shown in SEQ ID NO: 9, and corresponding amino acid sequence, as shown in SEQ ID NO: 10, of the HGF variant HGF/NK1, encoded by the 1.7 kb cDNA.

FIG. 10 shows a terminal portion of the coding sequence and part of the 3'-untranslated (3'-ut) region (SEQ ID NO: 11 and SEQ ID NO: 12) of the 2.2 kb cDNA encoding HGF/NK1. The sequence up to and including nucleotide 624 are the same for the 1.7 and 2.2 cDNA The sequence of the 3'-ut is not present in the cDNA molecules or transcripts corresponding to HGF or HGF/NK2 and differs, in part, from the 3' untranslated region in the 1.7 kb HGF/NK1 cDNA insert. The two underlined sequences correspond to primers used in a PCR reaction to generate a DNA fragment which was employed in Northern blot analysis to detect a HGF/NK1 transcript (see FIG. 11). Dashes indicate a short stretch of undetermined sequence.

Figure 11:
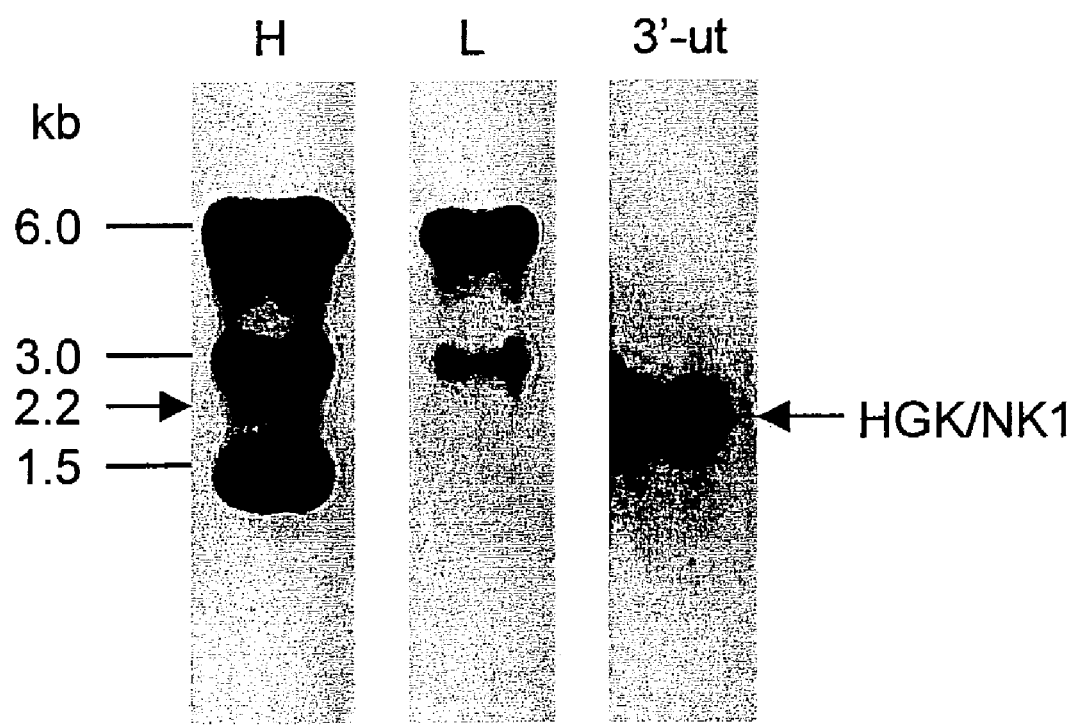

FIG. 11 represents a Northern blot analysis of RNA from M426 cells, using probes that can differentiate HGF/NK1 transcript(s) from molecules encoding HGF or HGF/NK2. Five μg of poly (A)+RNA from M426 cells were electrophoresed on 1% agarose gels, and Northern blots were hybridized with either a HGF heavy (H) or light (L) chain probe or a probe consisting of the 3'-ut sequence from the HGF/NK1 cDNA shown in FIG. 10. Lane 1 was screened with a heavy chain (H), lane 2 with a light chain (L) and lane 3 with the HGF/NK1 3'-ut probe. The sizes in kilobases (kb) of the HGF/NK1 transcript and other HGF-related transcripts are indicated. Arrows point to the 2.2 kb HGF/NK1 transcript.

Figure 12:
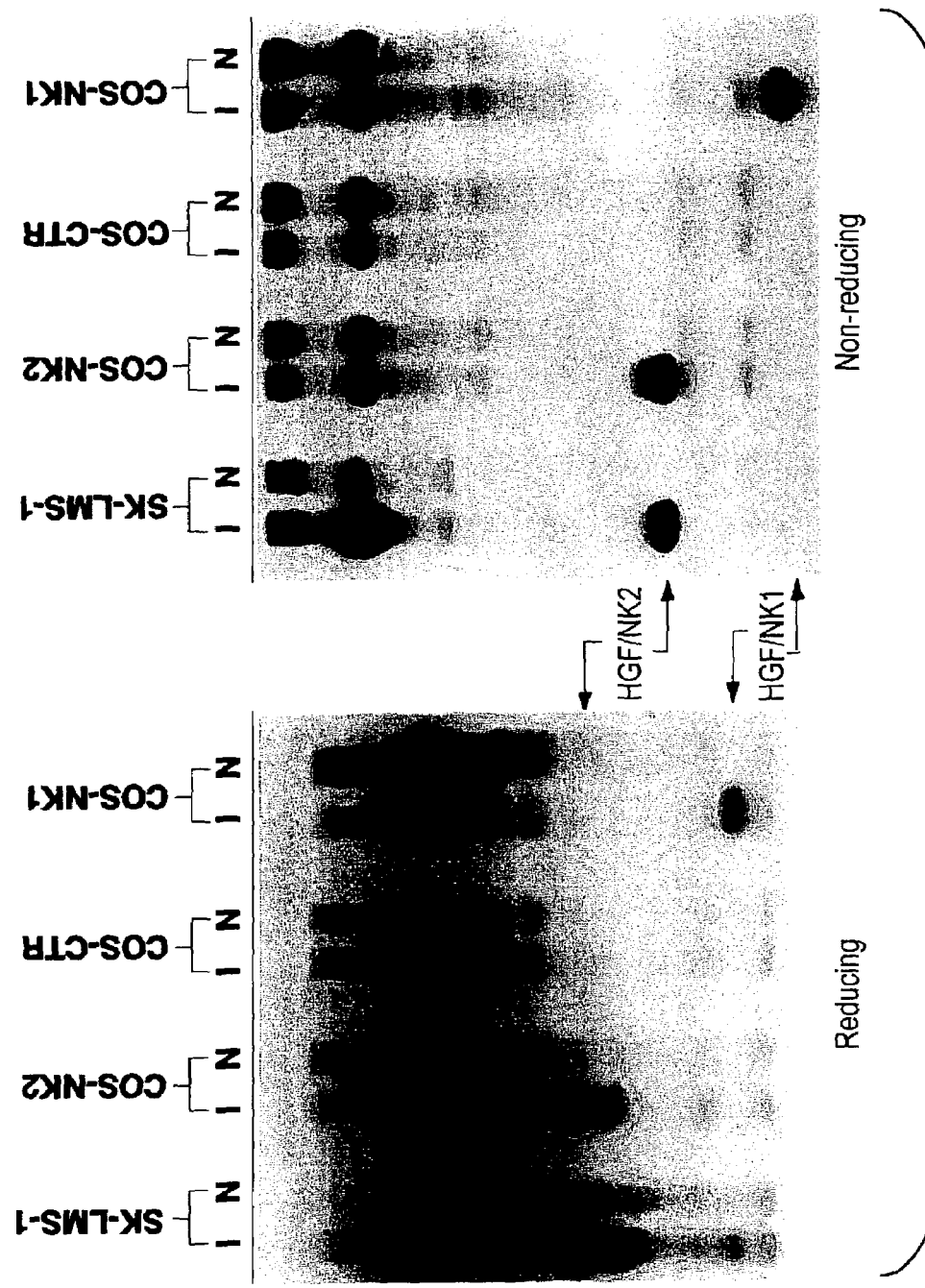

FIG. 12 shows an autoradiogram of $[^{35}S]$-labeled proteins immunoprecipitated from metabolically labeled SK-LMS-1 cells as well as COS-1 cells transfected with either the HGF/NK1 or HGF/NK2 coding sequence or a vector control (designated COS-CTR). Protein pelleted with antiserum raised against HGF was resolved by SDS-PAGE (12.5% and 14% polyacrylamide for non-reducing and reducing gels, respectively), and the dried gels were exposed to X-ray film. A band corresponding to HGF/NK1 was evident at ~20 kD under non-reducing conditions and ~23 kD under reducing conditions; HFG/NK2 was observed as illustrated in FIG. 5.

Figure 13:
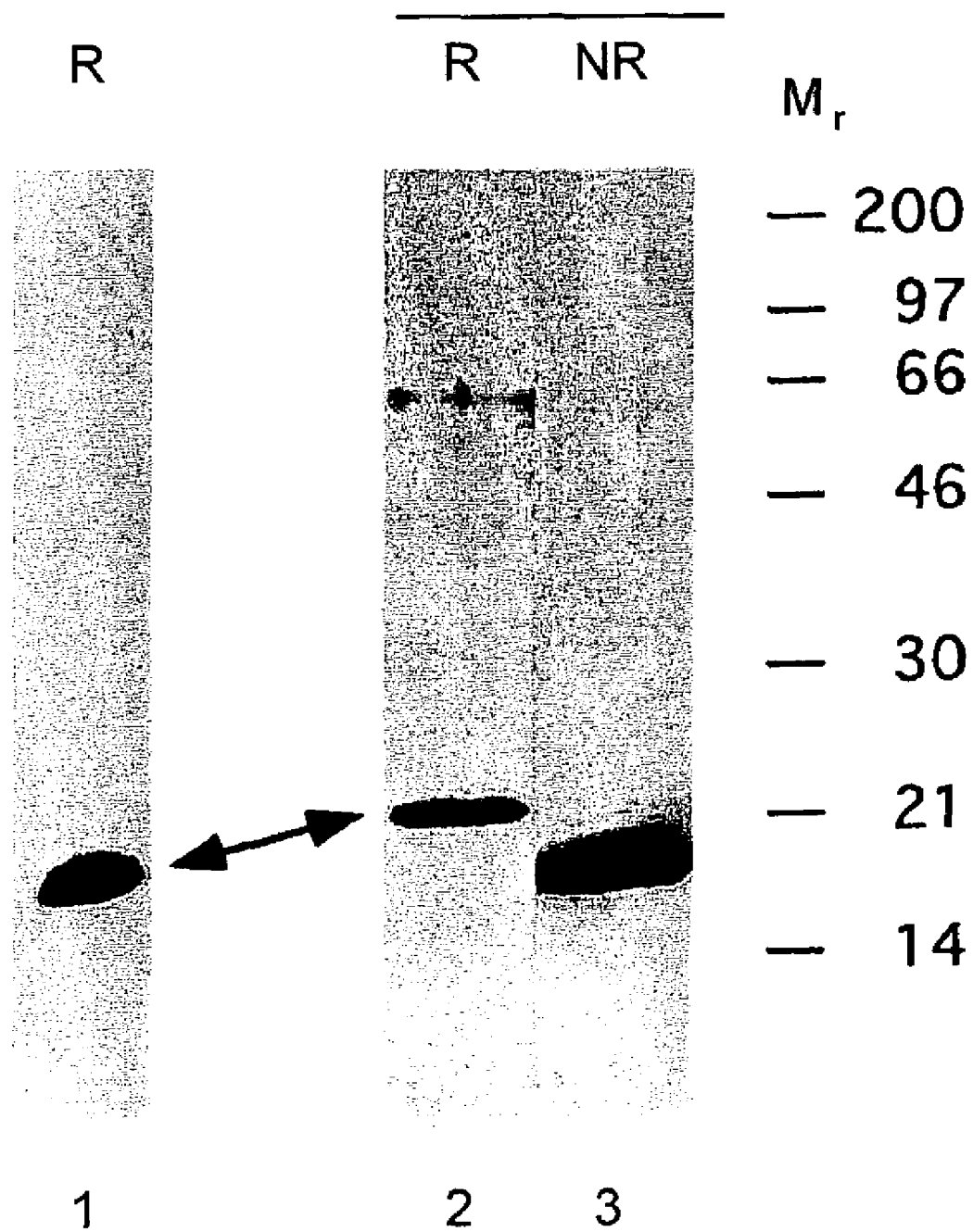

FIG. 13. Silver-staining and immunoblot analysis of purified, baculovirus-expressed HGF/NK1. Protein was resolved by electrophoresis in 12.5% polyacrylamide SDS gels under reducing (R) or non-reducing conditions, and detected by silver-staining (lane 1, 150 ng) or immunoblot analysis (lanes 2, 200 ng, and 3, 100 ng). Positions of molecular mass markers is indicated at the right.

FIG. 14. Effect of HGF/SF and HGF/NK1 on DNA synthesis by B5/589 cells.

Figure 14A:
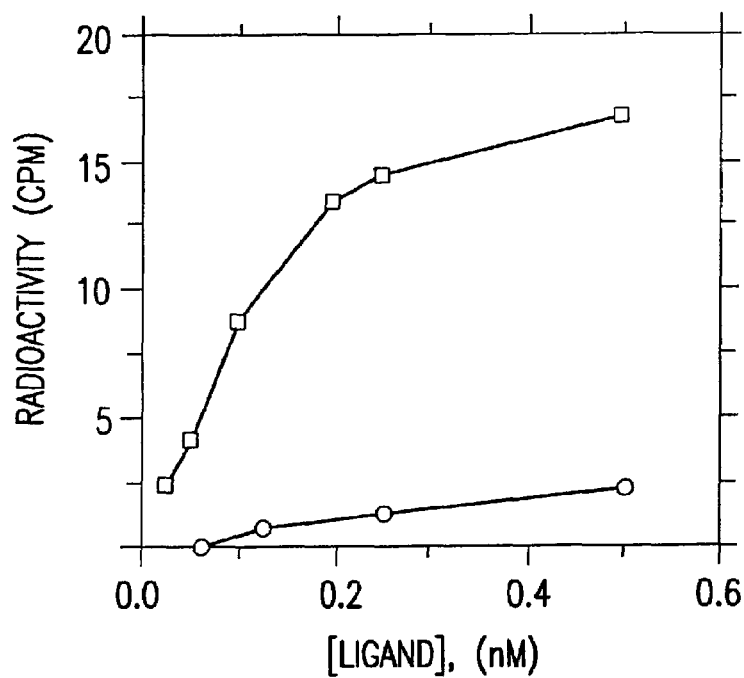

FIG. 14(A). Stimulation of $[^3H]$thymidine incorporation by HGF/SF (squares) or HGF/NK1 (circles). Mean values of triplicate measurements from one of several representative experiments are expressed as cpm×$10^{-3}$. Standard deviations were <10% and background was ⁻3200 cpm.

FIG. 14 (B). Percentage of maximal stimulation in the presence of increasing concentrations of HGF/NK1 and a fixed amount of HGF/SF (0.1 nM, circles) or EGF (0.4 nM, squares). Precision, background and absolute cpm values were comparable to those in A.

FIG. 15 is a chart showing the dose response of B5/589 cells to various concentrations of HGF/SF, HGF/NK1, and HGF/NK2, in the presence of insulin. The HGF/NK1 and HGF/NK2 variants were expressed in bacteria.

Figure 16:
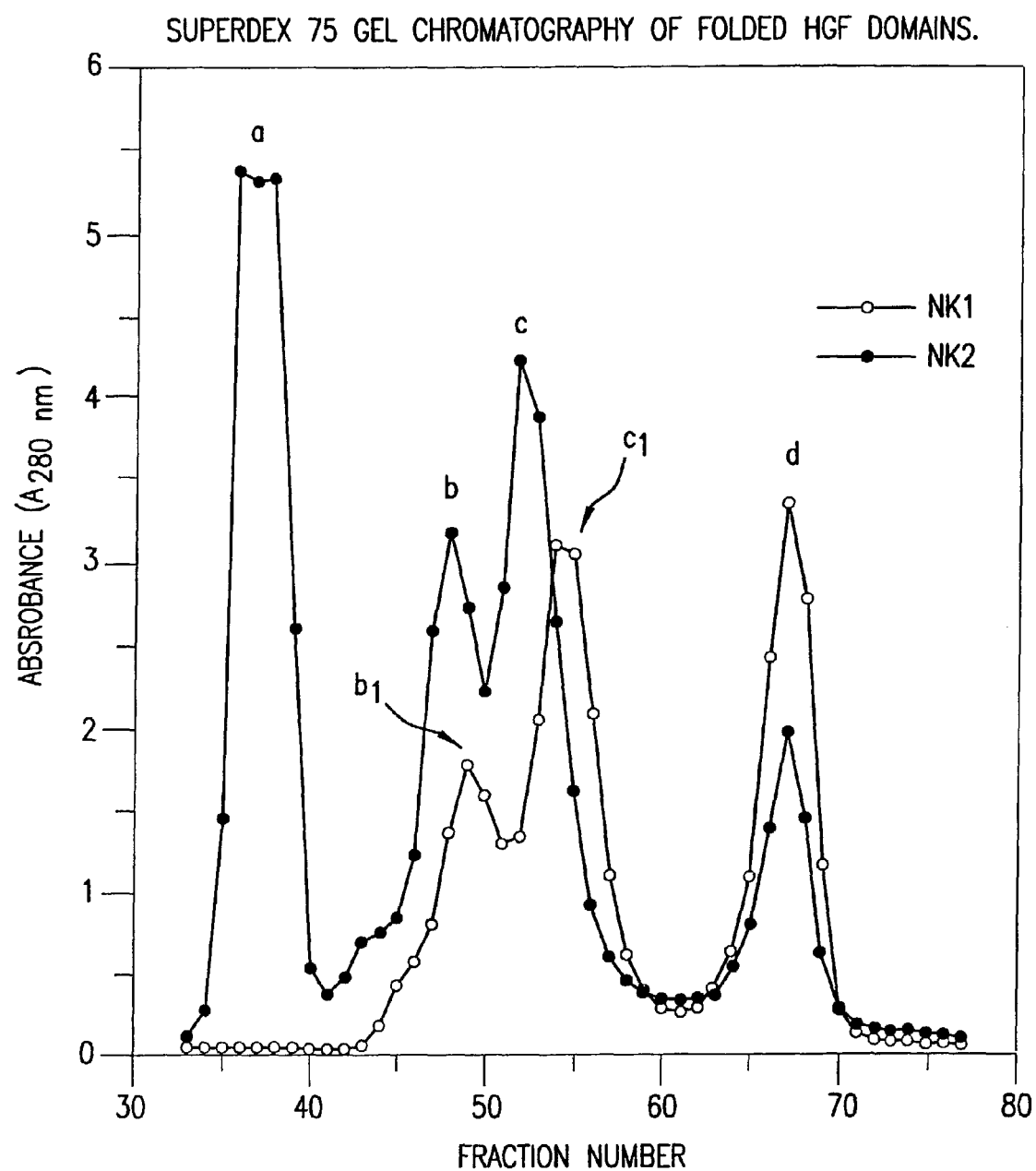

FIG. 16 shows the results of a gel chromatography of folded HGF domains.

Figure 17:
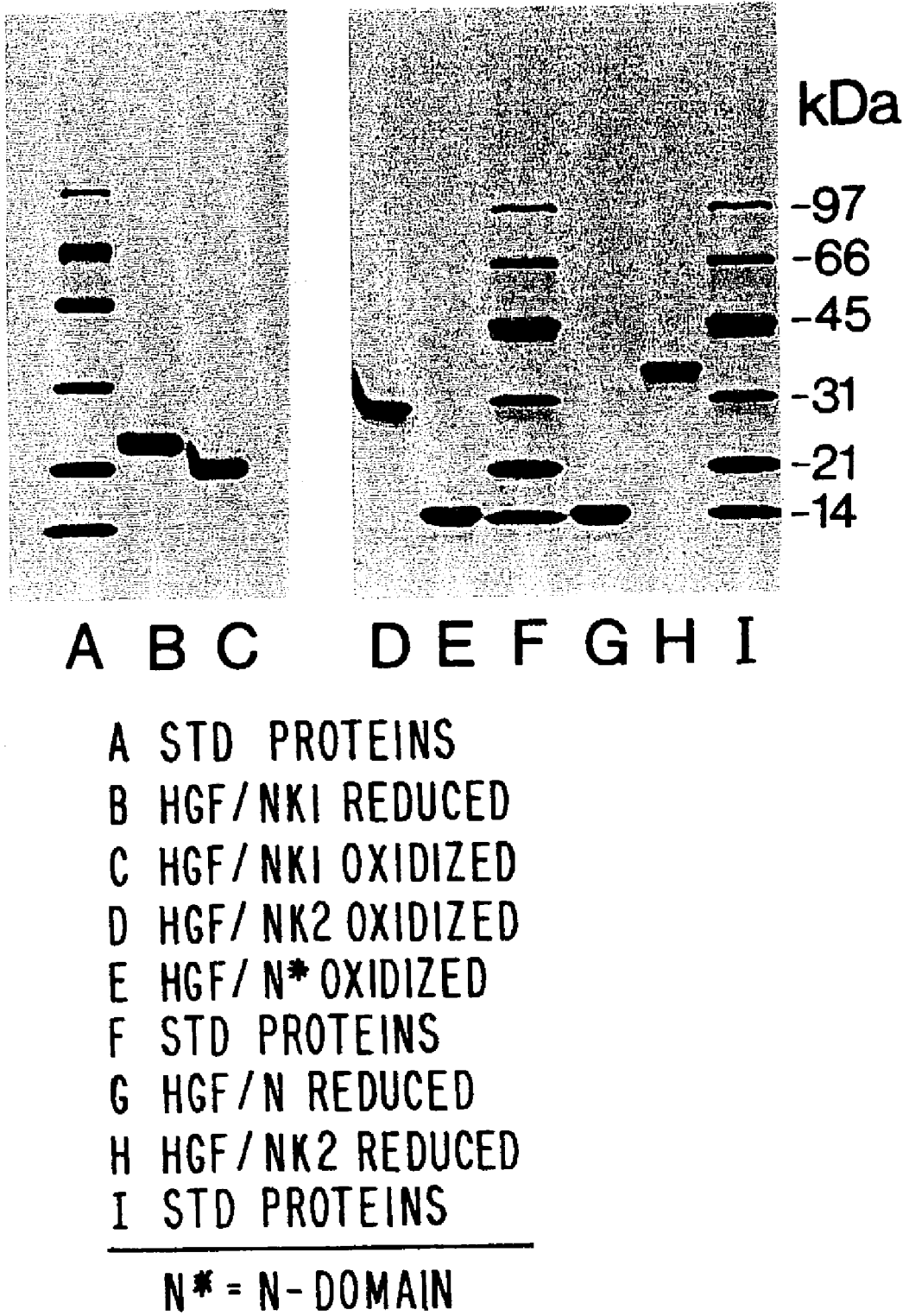

FIG. 17 shows the results of SDS-PACE of HGF/NK1 and HGF/NK2.

Figure 18:
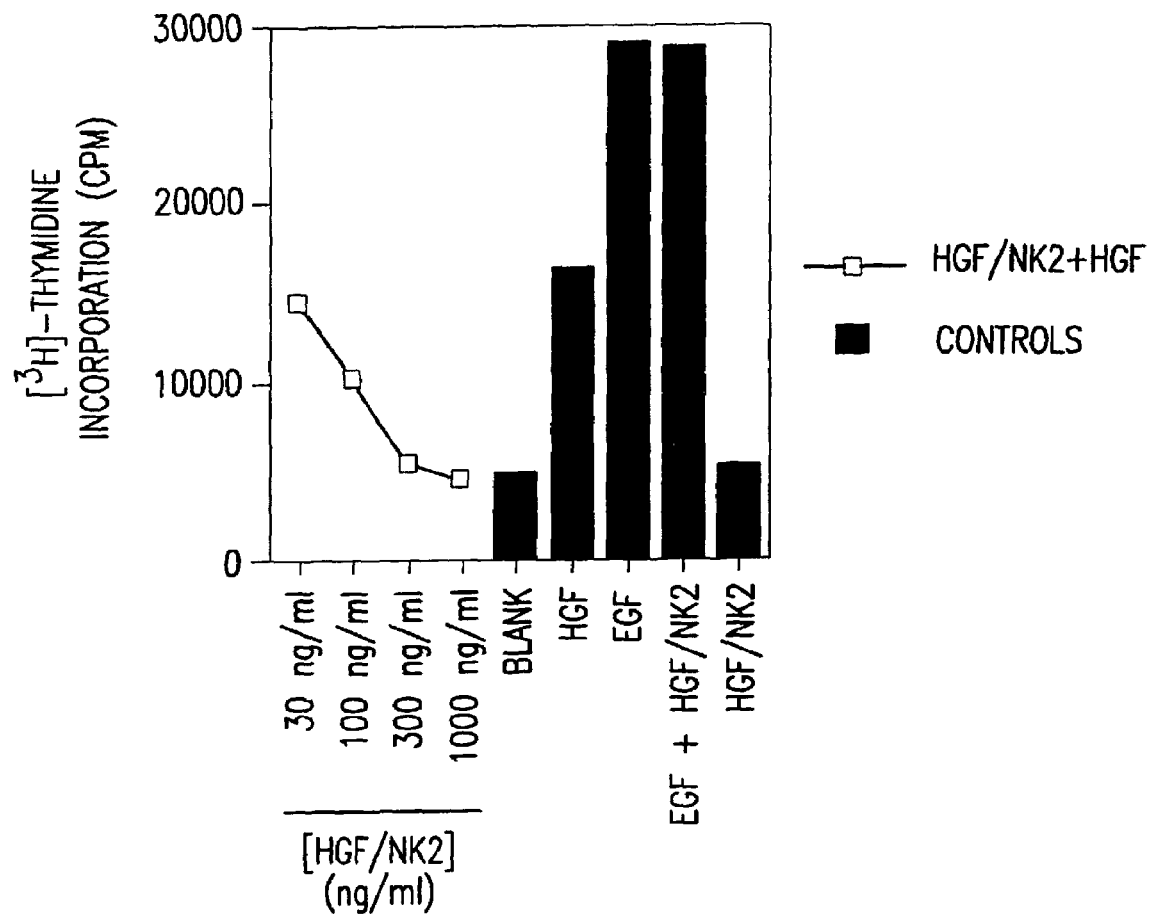

FIG. 18 shows specific inhibition of HGF mitogenic activity by bacterially expressed HGF/NK2 in B5/589[$^3$H]-thymidine incorporation bioassay. The assay was performed with a fixed concentration of HGF (15 ng/ml) and varying concentrations of HGF/NK2. Controls included: no supplement (BLANK), HGF alone (15 ng/ml) and EGF alone (10 ng/ml). Also, note that HGF/NK2 itself did not stimulate DNA synthesis at any of the concentrations tested (30, 100, 300 or 1000 ng/ml), nor did it inhibit EGF activity (shown here is activity of EGF at 10 ng/ml in the presence of HGF/NK2 at 300 ng/ml).

DETAILED DESCRIPTION OF THE INVENTION

The present invention relates to a substantially pure Hepatocyte Growth Factor ("HGF") variant that is a truncated form of HGF.

By the term "HGF" is meant "Hepatocyte Growth Factor" that is capable of specifically binding to the c-met oncogene product, as described in Bottaro et al., *Science* 251: 802-804 (1991). HGF refers to the mature HGF polypeptide having six domains: amino terminal, Kringle 1, Kringle 2, Kringle 3, Kringle 4 and serine protease domains, and has the amino acid sequence set forth in Rubin et al., *PNAS USA* 88: 415-419 (1991) and Miyazawa et al., *Biochem. Biophy. Res. Comm.* 163: 967-973 (1989). HGF is identical to scatter factor. The "biological activity" of HGF is any mitogenic, motogenic or morphogenic activities induced by HGF. It is well-accepted in the art that the term "mitogenesis" means cell growth, "motogenesis" means cell motility, and "morphogenesis" means a change in cell or tissue structure or organization.

The biological activity of HGF or the HGF variants of the present invention may be determined in any in vitro or in vivo assay well-known to the skilled artisan. For instance, such an assay may involve testing the ability of an HGF molecule to induce DNA synthesis in rat hepatocytes in primary cultures, as discussed in a review article by Rubin et al., *Biochem. et Biophysica Acta* 1155: 357-371 (1993) and the references reviewed therein, which are all hereby incorporated by reference. For example, DNA synthesis can be determined by measuring incorporation of [$^3$H] thymidine into DNA, with appropriate controls, according to well known methods in the art. Biological activity also may be assessed through in vivo assays using animal models, according to methods well-known in the art. For instance, one can induce liver or kidney damage in rats or other suitable mammals by treatment with toxins, such as carbon tetrachloride, D-galactosamine, alpha-naphthylisothiocyanate, $HgCl_2$, cisplatin or by partial hepatectomy. Such rats can then treated with HGF or the HGF variants of the present invention, pursuant to a carefully planned protocol and then sacrificed. Livers or kidneys are then observed for evidence of regeneration and changes in serum chemistry are noted. See, Ishiki et al., *Hepatology* 16: 1227-1235 (1992); Kawaida et al, *PNAS USA* 91: 4357-4361 (1994); Miller et al., *Am. J. Physiol.* 266: F129-F134 (1994), all of which are hereby incorporated by reference.

The term "substantially pure" is intended to mean a protein that is free of other proteins with which it is associated in nature.

A "truncated form of HGF" is a fragment or shortened form of the mature polypeptide of HGF. In one embodiment, such truncated form of HGF is encoded by an alternative HGF transcript that specifies a sequence that includes the N-terminal and first two kringle domains of HGF. This truncated form of HGF, called HGF/NK2, specifically inhibits HGF-induced mitogenesis. See Example 5, below. HGF/NK2 is synthesized in cells that also normally synthesize HGF. It is characterized by a molecular weight of about 34 kd, as determined by SDS-PAGE under reducing conditions. The molecule lacks intrinsic mitogenic activity but specifically inhibits HGF-induced mitogenesis by competing with the growth factor for binding to the HGF receptor. See Example 5. Thus, HGF/NK2 is an HGF antagonist. The term "antagonist" means a molecule that is lacking intrinsic stimulatory activity but can inhibit the activity of another molecule (agonist), which is capable of eliciting a specific biological effect.

The HGF/NK2 and HGF protein sequences are 99% identical throughout the entire length of the HGF/NK2. The truncated HGF and allelic variants thereof represent the product of an alternative transcript derived either from the same genetic locus encoding HGF or from a recently duplicated gene copy. This conclusion is supported by findings that not only the HGF/NK2 coding sequence but its upstream 5'-untranslated region are identical to that of the HGF cDNA. Further evidence shows that the K2 (kringle two) sequence is contiguous in human genomic DNA with the exon containing the termination codon and polyadenylation signal for the HGF/NK2 transcript (FIG. 4(A)). FIG. 3 shows the cDNA coding sequence and corresponding amino acid sequence of HGF/NK2.

In another embodiment, the invention relates to a substantially pure HGF variant, HGF/NK1, that is a truncated form of HGF comprising the N-terminal and the first kringle domain of HGF, and that is a partial agonist. HGF/NK1 is also synthesized by cells that normally synthesize HGF and also results from alternatively spliced transcripts derived from the HGF gene. Analysis of baculovirus-expressed HGF/NK1 isoforms demonstrates that HGF/NK1 possesses the heparin-binding properties of HGF and partial agonist activity in mitogenic and scattering assays. However, at a 20-40 fold molar excess, HGF/NK1 antagonizes HGF-dependent DNA synthesis. See Example 10, below. The term "agonist" means a molecule that elicits a specific biological effect through a direct and specific interaction with a receptor. HGF/NK1 is a "partial agonist" because, while it stimulates mitogenesis as a consequence of its interaction with the HGF receptor, the maximal effect attainable is lower than that observed with the prototypical agonist, HGF, and/or the concentration required to achieve this maximal effect is higher than that required for the maximal effect of HGF. A partial agonist also may be viewed as a "partial antagonist" if it can inhibit the activity of the prototypical agonist at an appropriate concentration. Typically, such inhibition would be observed with a partial agonist/antagonist molar concentration that is at least 10-100 times greater than that of the agonist.

Thus, an HGF variant is a partial agonist if it stimulates at least 20%, preferably at least 50%, more preferably at least 65%, and most preferably at least 80% of the maximal mitogenic response to HGF in an established bioassay, such as those described and exemplified herein.

Two different species of HGF/NK1 have been discovered. That is, differential screening of an M426 human fibroblast cDNA library with HGF heavy and light chain probes led to the isolation of several clones which hybridized only to the heavy chain probe. Restriction enzyme analysis indicated that multiple sequences were encoded by the different clones. Two clones (pH46 and pH50, ATCC accession numbers PTA-894 and PTA-895, respectively) contained 2.2 kb and 1.7 kb cDNA, respectively, and exhibited related enzyme restriction maps. Sequence analysis revealed that each encoded a truncated version of HGF consisting of the signal peptide, NH2-terminal domain and the first kringle domain (K1). Their sequences were completely divergent downstream from K1, although both open reading frames predicted only a few amino acids beyond K1. See FIGS. 9 (as shown in SEQ ID NO: 10) and 10 (as shown in SEQ ID NO: 11). The cDNA coding sequence (as shown in SEQ ID NO: 9) and corresponding amino acid sequence (as shown in SEQ ID NO: 10) of 1.7 kb HGF/NK1 species is set forth in FIG. 9. The terminal portion of the coding sequence and part of the 3'-untranslated (3'-ut) region (as shown in SEQ ID NO: 11) of the 2.2 kb cDNA encoding HGF/NK1 is set forth in FIG. 10.

The HGF variants of the present invention are intended to include "analogs" of such HGF variants. Analogs may contain minor sequence variations of the above described HGF variants that arise due to natural variation within the population of the cells from which the variant is isolated. Analogs also include amino acid insertions, deletions, or substitutions in the variants that do not substantially affect their properties. Sequence variants can be prepared by standard methods of site-directed mutagenesis. Deletion variants lack one or more residues of the native HGF variant that are not essential for the HGF variant's biological activity. Substitutional variants typically contain the exchange of one amino acid for another at one or more sites within the truncated variant. Substitutions preferably are conservative, that is, one amino acid is replaced with one of similar shape and charge. Conservative substitutions are well known in the art and include, for example, the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Analogs according to the invention can be constructed using any technique known in the art. For instance, site-directed mutagenesis is described in Sambrook et al., *Molecular Cloning: A Laboratory Manual*, second edition, Cold Spring Harbor Laboratory Press, New York (1989). A particularly preferred method of preparing analogs of the HGF variants of the invention involves oligonucleotide-directed mutagenesis, as described in Adelman et al., *DNA* 2: 183 (1983) and Sambrook et al., supra. Yet another method of producing analogs of the HGF variants of the invention involves PCR mutagenesis, as described in U.S. Pat. No. 4,683,195 and in *Current Protocols in Molecular Biology*, Ausubel et al. eds. Greene Publishing Associates and Wiley-Interscience, Vol. 2, Chapter 15, 1991.

In a preferred embodiment, the invention relates to an analog of an HGF variant of the present invention that is HGF/NK2 (C214A). HGF/NK2(C214A) was derived from expression plasmid, pET11-HGF/NK2, using polymerase chain reaction to substitute alanine for cysteine-214 in HGF/NK2. See Example 9, below, wherein the production of this analog is discussed.

Insertional variants are fusion proteins, which may include hybrid proteins containing sequences from other proteins and polypeptides.

In another preferred embodiment, an HGF variant according to the present invention comprises the amino acids of such HGF variant together with a toxin. See generally, Siegall, C., *Cancer* 74: 1006 (1994) and references cited therein. An example of such molecule is HGF/NK2-Saporin, which can be produced according to procedures set forth in Lappi et al., *Biochem. Biophys. Res. Commun.* 160: 917-23 (1989), hereby incorporated by reference.

In yet another preferred embodiment, the analog of the HGF variant of the present invention is an IgG/non-IgG fusion protein, as described in U.S. patent application Ser. No. 08/189,552, hereby incorporated by reference. See also, La Rochelle et al., *J. Cell Biol.* 129: 357-366 (1995). Such fusion protein comprises (A) an IgG sequence, (B) a nonantibody sequence covalently joined to the aminoterminal end of the IgG sequence and (C) a heterologous signal peptide that is covalently joined to the aminoterminal of the nonantibody sequence, wherein (i) the IgG sequence consists essentially of a hinge region, a $CH_2$ domain and a $CH_3$ domain, in that order, that IgG sequence lacking a $CH_1$ domain, and (ii) the nonantibody sequence comprises an HGF/NK1 or HGF/NK2 variant of the invention.

In a particularly preferred embodiment, the IgG sequence is cDNA encoding the HFc portion of the mouse IgG heavy-chain at the hinge region, which includes $CH_2$ and $CH_3$ domains. In accordance with the teachings of U.S. patent application Ser. No. 08/189,552, such chimera is produced by subcloning DNA sequences coding for the fusion protein into an expression vector which is used to transfect mammalian cells. General techniques for producing fusion proteins comprising antibody sequences are described in Coligan et al. (eds.), CURRENT PROTOCOLS IN IMMUNOLOGY, at pp. 10.19.1-10.19.11 (Wiley Interscience 1992), the contents of which are hereby incorporated by reference. See also METHODS: A COMPANION TO METHODS IN ENZYMOLOGY, Volume 2 (No. 2), Academic Press (1991), and ANTIBODY ENGINEERING: A PRACTICAL GUIDE, W. H. Freeman and Company (1992), in which commentary relevant to production of fusion proteins is dispersed throughout the respective texts.

Thus, the first step in the construction of fusion proteins is to subclone portions of the fusion proteins in cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance. Suitable cloning vectors are described by Sambrook et al. (eds.), MOLECULAR CLONING: A LABORATORY MANUAL, Second Edition (Cold Spring Harbor Press 1989) (hereafter "Sambrook"); by Ausubel et al. (eds.), CURRENT PROTOCOLS IN MOLECULAR BIOLOGY (Wiley Interscience 1987) (hereafter "Ausubel"); and by Brown (ed.), MOLECULAR BIOLOGY LABFAX (Academic Press 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

As noted above, the DNA sequence encoding the Ig portion of a fusion protein within the present invention preferably encodes an Ig heavy chain. More preferably, such a DNA sequence encodes the hinge, $CH_2$ and $CH_3$ domains of IgG. Immunoglobulin DNA sequences can be obtained using the polymerase chain reaction (PCR) as described, for example, by Coligan et al. (eds.), CURRENT PROTOCOLS IN IMMUNOLOGY, pages 10.20.1-10.20.8 (Wiley Interscience 1992) (hereafter "Coligan").

By one approach, antibody DNA sequences are amplified from RNA of cells that synthesize an immunoglobulin. Larrick et al., "PCR Amplification of Antibody Genes," in 2 METHODS: A COMPANION TO METHODS IN ENZYMOLOGY 106 (1991). Briefly, total RNA is isolated from immunoglobulin-producing cells using standard techniques. See Ausubel at pages 4.1.2-4.2.8. Poly A+ RNA then is isolated from total RNA using the standard technique of oligo-dT column chromatography as described, for instance, by Sambrook. Single-stranded cDNA molecules then are synthesized from poly A+ RNA using reverse transcriptase. Techniques for synthesizing cDNA are described in each of Sambrook, Ausubel, and Coligan. Moreover, commercially available kits can be used to synthesize cDNA molecules. For example, such kits are available from GIBCO/BRL (Gaithersburg, Md.), Clontech Laboratories, Inc. (Palo Alto, Calif.), Promega Corporation (Madison, Wis.) and Stratagene Cloning Systems (La Jolla, Calif.).

The PCR reaction is performed with the single-stranded cDNA template and a mixture of oligonucleotide primers. The design of oligonucleotide primers can be based upon the DNA sequence of the immunoglobulin of interest. Alternatively, oligonucleotide primers can be designed based on information from a database of immunoglobulin amino sequences, such as Kabat et al., SEQUENCES OF PROTEINS OF IMMUNOLOGICAL INTEREST, U.S. Department of Health and Human Services (1983), taking into account degeneracies for each amino acid. Oligonucleotide synthesis and purification techniques are described in Sambrook and Ausubel, respectively. The PCR procedure is performed via well-known methodology. See, for example, Ausubel, Coligan, and Bangham, "The Polymerase Chain Reaction: Getting Started," in PROTOCOLS IN HUMAN MOLECULAR GENETICS (Humana Press 1991). Moreover, PCR kits can be purchased from companies such as Stratagene Cloning Systems (La Jolla, Calif.) and Invitrogen (San Diego, Calif.).

Alternatively, immunoglobulin-encoding DNA sequences can be synthesized using PCR with cloned immunoglobulins. DNA sequences encoding HGF/NK1 or HGF/NK2 can be synthesized using PCR with RNA isolated from cells that produce such variants.

Alternatively, DNA sequences encoding HGF/NK1 or HGF/NK2 can be obtained using PCR with an HGF/NK1 or HGF/NK2 cDNA template.

DNA sequences that encode heterologous signal peptides can be obtained via PCR with RNA isolated from cells that produce the HGF variants of the present invention. Such DNA sequences also can be obtained by isolating fragments of HGF/NK1 or HGF/NK2 cDNAs that encode a signal peptide.

Alternatively, DNA sequences encoding signal peptides can be obtained by synthesizing oligonucleotides that encode known signal peptide amino acid sequences. Such amino acid sequences are disclosed, for example, by Darnell et al., supra, and Wallis et al., THE BIOCHEMISTRY OF THE POLYPEPTIDE HORMONES, page 212 (John Wiley & Sons 1985). Techniques for oligonucleotide synthesis are disclosed, for example, by Ausubel at pp. 2.11.1-2.12.5. Also, see generally Eckstein et al. (ed.), OLIGONUCLEOTIDES AND ANALOGUES: A PRACTICAL APPROACH (IRL Press 1992).

DNA sequences encoding a heterologous signal peptide are subcloned in frame with DNA sequences encoding the N-terminus of an HCF variant of the present invention, while DNA sequences encoding the HGF variant are subcloned in frame with the N-terminus of the antibody portion of the fusion protein. Subcloning is performed in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are described by Sambrook and Ausubel, and are well-known in the art. Techniques for amplification of cloned DNA in bacterial hosts and isolation of cloned DNA from bacterial hosts also are well-known. Id.

The cloned fusion protein is cleaved from the cloning vector and inserted into an expression vector. Suitable expression vectors typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

A fusion protein of the present invention is expressed in either eukaryotic or prokaryotic cells. Suitable prokaryotic expression systems are described in Example 9, below. E. coli and B. subtilis are examples of two suitable prokaryotic host cells. Prokaryotic expression of fusion proteins, in accordance with the invention, would increase solubility of the expressed product, would facilitate purification and favor secretion.

However, preferably the fusion protein of the present invention is expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH/3T3; ATCC CRL 1658). Preferably, the mammalian host cells are NIH-3T3 cells.

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., J. Molec. Appl. Genet. 1: 273 (1982)); the TK promoter of Herpes virus (McKnight, Cell 31: 355 (1982)); the SV40 early promoter (Benoist et al., Nature 290: 304 (1981)); the Rous sarcoma virus promoter (Gorman et al., *Proc. Nat'l Acad. Sci. USA* 79: 6777 (1982)); and the cytomegalovirus promoter (Foecking et al., *Gene* 45: 101 (1980)).

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10: 4529 (1990); Kaufman et al., *Nucl. Acids Res.* 19: 4485 (1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described by Sambrook, by Ausubel, by Bebbington, "Expression of Antibody Genes in Nonlymphoid Mammalian Cells," in 2 METHODS: A COMPANION TO METHODS IN ENZYMOLOGY 136 (1991), and by Murray (ed.), GENE TRANSFER AND EXPRESSION PROTOCOLS (Humana Press 1991).

Stable transformants that produce a fusion protein can be identified using a variety of methods. For example, stable transformants can be screened using an antibody that binds either to the nonantibody portion of the fusion protein or to the antibody portion of the fusion protein. The use of immunoprecipitation to identify cells that produce fusion proteins is routine in the art of the invention.

After fusion protein-producing cells have been identified, the cells are cultured and fusion proteins are isolated from culture supernatants. As described, for example, by Coligan, isolation techniques include affinity chromatography with Protein-A Sepharose, size-exclusion chromatography and ion exchange chromatography. Protein A preferably is used to isolate fusion proteins from supernatants.

IgG HGF variant chimera and fusion proteins according to the present invention, can be used, for instance, in immunoprecipitation techniques and in assays for screening inhibitors of HGF-receptor binding.

In yet another embodiment, the HGF variants of the invention are used for the preparation of peptide mimetics. Mimetics are peptide-containing molecules which mimic elements of protein secondary structure. See, for example, Johnson et al.,"Peptide Turn Mimetics" in BIOTECHNOLOGY AND PHARMACY, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions, such as those of a ligand and receptor. A peptide mimetic of the present invention would, when administered to a host, mimic the biological activity of the HGF variant. The mimetic can then be conjugated to a carrier protein for use, for example, in stimulating or inhibiting mitogenesis in cells bearing HGF receptors.

The HGF variant protein to which the invention relates can be isolated from conditioned medium of a human leiomyosarcoma cell line as well as other cell lines, for example, M426 fibroblast line, substantially free from other proteins.

Pursuant to the instructions presented herein, and applying methods well known to the skilled artisan in the field of the invention, a biologically active form of HGF variant of the present invention can be obtained by a combination of protein purification steps that include concentrating the conditioned medium, applying the concentrate to heparin supports, for example, heparin-Sepharose resins, and eluting the HGF variant with an increasing salt gradient. Substantially purified HGF variant is realized after the heparin bound eluate is fractionated over a sizing column, for example, TSK-G3000, in order for the HGF variant to be separated from any remaining components in the eluate. "Biological activity" has the definition set forth above and can be assessed using any of the in vitro or in vivo assays described and exemplified herein.

In another embodiment, the present invention relates to a method of producing a substantially pure and biologically active HGF variant comprising the steps of:

(i) disrupting HGF variant-producing bacteria that have been cultured in a culture medium under conditions such that HGF variant is expressed, so as to produce a first HGF variant protein-containing suspension;

(ii) recovering the protein from said first suspension and, washing and solubilizing said recovered protein, wherein said solubilizing is performed with a denaturant and reducing agent, and wherein a second HGF variant protein-containing suspension is produced;

(iii) fractionating said proteins in said second suspension by sizing chromatography with a solvent containing a denaturant and a reducing agent;

(iv) removing said denaturant from the fractions of step (iii) and pooling fractions containing denatured HGF variant;

(v) purifying the HGF variant protein in the pooled fractions by reverse phase chromatography;

(vi) lyophilizing the purified HGF variant proteins of step (v) and redissolving said lyophilized proteins with denaturing and reducing agents;

(vii) serially diluting and then incubating said redissolved lyophilized proteins in refolding buffer, and then removing said denaturant by dialysis, so as to produce biologically active proteins;

(viii) concentrating and then purifying said dialyzed proteins by sizing chromatography, so as to produce several fractions containing biologically active HGF variant; and (ix) pooling and then concentrating said fractions containing biologically active HGF variant.

Example 9, shows that a properly folded and biologically active HGF variant can be found in the concentrate of step (ix) above. See also, FIG. 16 that shows that peak c contains the biologically active folded protein.

The bacteria of this method can be any bacteria known in the art for use in expression systems. See *Invitrogen Corp., Catalog*, San Diego, Calif. (1994). In a preferred embodiment, the bacteria of this method is *Bacillus subtilis*, in a most preferred embodiment, the bacteria is *E. coli*. After the bacteria has been transformed with plasmid DNA encoding the HGF variant, it is cultured pursuant to protocols well-known in the art. For instance, it can be cultured in any medium suitable for maintaining the growth of such bacteria. Such medium might contain, among other ingredients, glucose, yeast extract, dibasic potassium phosphate, ampicillin and trace metals. HGF variant producing culturing conditions include fermentation at an appropriate temperature and with proper aeration, according to methods well-known in the art. Bacteria producing HGF variant is then harvested, at which point the cells can be frozen for future use. The bacteria is then resuspended and then disrupted using any suitable method, such as the application of pressure or detergent and sonication. Afterwards, the suspension containing the disrupted cells is centrifuged to recover the protein in a pellet. The pellet is then washed and the protein is solubilized with a denaturant and reducing agent. Suitable denaturants and reducing agents are well-known to the skilled artisan and include, but are not limited to Tris-HCl, guanidine-HCl and dithiothreitol. Concentrations are set according to standard protocols in the art. The resultant solution is then clarified by centrifugation. The denaturant is then removed from the solution containing the proteins and then the solution is subjected to sizing chromatography using a solvent containing a denaturant and reducing agent. The denaturant is then again removed and selected fractions are pooled. The pooled fractions may then be frozen for future use. The pooled protein fractions are then acidified and then further purified using reverse phase chromatography. The protein peak is then lyophilized and the lyophilized protein is redissolved in a denaturant and reducing agent. The redissolved protein is gradually diluted with a refolding buffer and then incubated. A suitable refolding buffer is a mixture of Tris-HCl, urea, oxidized glutathione and reduced glutathione, although other refolding buffers would be known to the skilled artisan. After incubation, this suspension is dialyzed and the proteins therein are concentrated by centrifugation and ultra filtration. The concentrated protein containing suspension is then fractionated by sizing chromatography and then selected fractions containing biologically active HGF variant are pooled and concentrated. The resultant concentrate contains biologically active HGF variant.

This method is exemplified in Example 9 and discussed in greater detail, below, in connection with prokaryotic expression of the HGF variants of the present invention.

Alternatively, the variant can be produced chemically or recombinantly using methods known in the art. For instance, DNA encoding HGF can be cleaved at the appropriate position by digestion with restriction enzymes, the properly cleaved DNA recovered, an oligonucleotide encoding the desired amino acid sequence and flanking regions such as polylinkers with blunt ends (or, instead of polylinkers, digesting the synthetic oligonucleotide with the restriction enzymes also used to cleave the HGF encoding DNA, thereby creating cohesive termini) synthesized, and the synthetic DNA ligated into an appropriate construct suitable for expression of the HGF variant protein.

The HGF variants of the present invention also can be prepared by recombinant expression. Accordingly, the invention relates to the cDNA clones that encode the truncated HGF variants, HGF/NK2 and HGF/NK1. By screening a M426 human lung fibroblast cDNA library with DNA probes specific for either the heavy or light chain region of HGF, several cDNA clones were identified that hybridized to the heavy but not the light chain probe. Two of these clones, having inserts of 1.2 or 1.6 kb, contain the coding sequence for the mitogenesis-inhibiting HGF variant, HGF/NK2; they differed from each other in the length of their 3'-untranslated sequence. However, as described above, two other clones contained inserts of 1.7 and 2.2 kb, respectively, and each encoded only the N-terminal and first kringle domain; they differed from each other in the terminal portion of their coding sequence (involving a few amino acid residues beyond the kringle domain) and in their 3'-untranslated region. The resultant truncated form of HGF, HGF/NK1, has a predicted molecular weight of approximately 20 kilodaltons. The Northern blot analysis of HGF expression in M426 and SK-LMS-1 human cell lines revealed a weak 2.2 kb band as well as a diffuse signed at 1.3-1.7 kb (FIGS. 2 and 11) which represent the transcripts corresponding to these relatively low abundance cDNAs encoding HGF/NK1 and HGF/NK2.

The present invention further relates to recombinant vectors containing DNA that encodes either of the human truncated HGF variants, HGF/NK1 or HGF/NK2. Possible vectors include plasmids, for example, pCDV-1 and other vectors such as pZIPneo, known in the art that either transiently (pCDV-1) or stably (pZIPneo) transform host cells in a manner which allows expression of the HGF variant. Examples of appropriate eukaryotic host cells include, for example, mouse fibroblasts and monkey epithelial cells. The bacculovirus as well as other eukaryotic or prokaryotic expression systems could be adapted for the production of the HGF variant.

Example 9 describes in detail the prokaryotic expression of NK1 and NK2. That is, Example 9 shows that HGF/N, HGF/NK1 and HGF/NK2 proteins were all well expressed in *E. coli*; each accumulating to about 10-20% of the total protein as evidenced by SDS-PAGE of cell extracts. The construct pET11-HGF/N encodes the polypeptide: $MG_{31} Q_{32} R_{33} \ldots R_{126} N_{127OH}$. The expressed proteins were insoluble and were extracted with Gdn-HCl and fractionated by gel filtration. The partially purified denatured proteins were folded into active proteins using an equilibrium dialysis scheme. In the first folding buffer a relatively low concentration of urea was included to prevent protein aggregation during the removal of the Gdn-HCl. Also included in the buffer was a glutathione based redox system to promote the formation of disulfide linkages from reduced protein by thiol-disulfide exchange reactions. The ratio of reduced to oxidized glutathione (5:1) and the concentration of urea (2.5M) were optimized in an empirical manner to the values indicated in Example 9.

After the dialysis stage, the proteins were concentrated by ultrafiltration then fractionated by gel filtration. Typical chromatograms for HGF/NK1 and HGF/NK2 are shown in FIG. 16. For HGF/NK1, there are two main protein peaks $b_1$ and $c_1$ and a third peak d, which contained non-proteinaceous material eluting at the included volume. Both peaks $b_1$ and $c_1$ contained monomeric protein; the difference in elution position was due to conformational differences as will be detailed below. Peak $c_1$ contained active folded protein and was the material used for further characterization. In the HGF/NK2 profile, peak a, eluting at the void volume, contained highly aggregated protein and peaks b and c correspond to the HGF/NK1 peaks $b_1$ and $c_1$, except that they eluted earlier as expected for a larger protein. Hence, peak c contained the active folded protein.

The elution profile for HGF/N was qualitatively similar to those shown in FIG. 16.

Example 10 describes the expression of HGF/NK1 in NIH/3T3 cells and in a baculovirus system.

Example 9 also shows that the prokaryotically expressed HGF variants of the present invention have biological activity that is comparable to that observed in HGF variants produced in eukaryotic systems. For instance, DNA synthesis was assayed by incorporation of [$^3$H]-thymidine into a trichloroacetic acid precipitable cell fraction as described in Rubin et al., *PNAS USA* 86: 802 (1989). Scatter factor activity was evaluated using MDCK cells. MDCK cell movement was observed as the dispersion or scatter of single cells from tightly grouped colonies, as described in Stoker and Perryman, *Cell Sci.* 77: 209-223 (1985). It was shown that both HGF/NK2 and HGF/NK1 bind to the high affinity HGF receptor, the c-met gene product, as evidenced by covalent affinity cross linking experiments using radiolabeled HGF variant. Both HGF variants stimulated receptor autophosphorylation and HGF/NK2 neutralized HGF mitogenic activity on B5/589 human mammary epithelial cells.

Thus, in view of the well-documented biological activities of the HGF variants of the invention, the present invention also relates to methods of inhibiting HGF induced mitogenesis in cells expressing the receptor for HGF. This method comprising contacting the cells with a mitogenesis-inhibiting amount of HGF/NK2, such that the HGF induced mitogenesis is inhibited when HGF/NK2 binds the receptor for HGF on the cells. By "inhibiting mitogenesis" is meant that DNA synthesis is reduced, with reference to the biological activity of HGF, as observed in a well-accepted bioassay, such as [$^3$H] thymidine incorporation assay. For instance, an HGF variant inhibits mitogenesis and is an HGF antagonist if it inhibits at least 50%, preferably at least 70%, more preferably at least 80% and most preferably at least 90% of the mitogenic activity of HGF, in an established bioassay, as described and exemplified herein. See FIG. 18.

Cells that express the receptor for HGF include, but are not limited to hepatocytes, melanocytes, endothelial cells, keratinocytes, sarcoma cells, cells of the gastro-intestinal and genito-urinary tract, breast cancer cells and various hematopoietic cells. What is meant by "mitogenesis-inhibiting amount" is that amount which inhibits at least 50%, preferably at least 70%, more preferably at least 80% and most preferably at least 90% of the mitogenic activity of HGF, in an established bioassay. Such a method of inhibiting mitogenesis would permit the treatment of pathologic conditions associated with the activation of the HGF receptor. These conditions include malignancies that are associated with HGF receptor activation, such as breast cancer, stomach and colon cancer. Other conditions include benign prostatic hyperplasia and psoriasis. However, as noted above, such method could also be used in in vitro and in vivo drug screening assays. For instance, a potential chemotherapeutic agent could be linked to HGF/NK1 or HGF/NK2 and then administered to a subject known to have a condition, such as a malignancy associated with the activation of the HGF receptor. HGF/NK1 or HGF/NK2 would act as a specific target of malignant cells bearing HGF receptors, thereby exposing such cells to the attached potentially toxic compound. Similar studies can be conducted in an in vitro, tissue culture assay. See, Siegall, C., supra.

The present invention also relates to methods of stimulating mitogenesis in cells expressing the receptor for HGF. This method comprises contacting such cells with a mitogenesis-stimulating amount HGF/NK1, such that mitogenesis is stimulated when HGF/NK1 binds the HGF receptor. As such, HGF/NK1 could be used as an HGF substitute for promoting angiogenesis, wound healing, cytoprotection and cell and tissue regeneration. See, Ishiki et al., *Hepatology* 16: 1227-1235 (1992); Kawaida et al, *PNAS USA* 91: 4357-4361 (1994); Miller et al., *Am. J. Physiol.* 266: F129-F134 (1994). HGF/NK1 also can be used as an HGF substitute to stimulate the production of hematopoietic cells, as disclosed in U.S. Pat. No. 5,362,716, herein incorporated by reference.

In one embodiment, the above method of stimulating mitogenesis can be used in ex vivo methods of culturing pancreatic islet cells for purposes of transplanting such cells into a subject. Such methods are taught with regard to HGF in U.S. patent application Ser. No. 08/235,394, hereby incorporated by reference.

What is meant by a "mitogenesis stimulating amount" would be readily understood by the skilled artisan relying upon the in vitro and in vivo assays described above and in the Examples below. Typical amounts would be in the range of 10-300 ng/ml, preferably 100-200 ng/ml.

In another embodiment, the present invention also relates to pharmaceutical compositions comprising therapeutically effective amounts of the truncated HGF variants described herein and pharmaceutically acceptable carriers. Suitable carriers are any carriers known to the skilled artisan for administration to humans that do not themselves induce any undesirable side effects such as the production of antibodies, fever, etc. Suitable carriers are typically large, slowly metabolized macromolecules that can be a protein, polysaccharide, a polylactic acid, a polyglycolic acid, a polymeric amino acid, amino acid copolymer or an inactive virus particle. Suitable carriers and their formulations are described in Remington's Pharmaceutical Sciences, 16th Ed. (1980) Mack Publishing Co., hereby incorporated by reference.

Pharmaceutical compositions according to the invention will typically contain an effective amount of HGF variant, for example, from about 0.5 to about 10 mg/ml, together with a suitable amount of carrier.

HGF variant containing compositions particularly well-suited for clinical administration include sterile hydratable powders such as lyophilized protein. Such composition may also contain a pharmaceutically acceptable salt so as to render the formulation isotonic.

Dosages and concentrations of the pharmaceutical compositions of the invention will necessarily vary depending upon the specific treatment in question. A typical effective dose in rat experiments is about 250 µg/kg, which is administered in an intravenous bolus injection. Dosages would be adjusted according to methods well-known in the art. See, for instance, Mordenti et al., *Pharmacuet. Res.* 8: 1351 (1991) and references cited therein, which teach interspecies scaling of drug dosages.

The HGF variants of the present invention may be administered by many different routes, such as topical, oral or parenteral, according to well known techniques in the art. If the pharmaceutical composition comprising the HGF variant of the invention is intended to be administered topically, so as to promote wound healing by stimulating mitogenesis, it may be in gel formulation, such as those set forth in EPA 312 208, and hereby incorporated by reference. Such gel formulations would contain a water soluble polymer capable of forming viscous aqueous solution (e.g. vinyl polymers) or non-water soluble swellable polymers (e.g. collagen) In one embodiment, the HGF variants of the present invention are covalently bonded to a hydrophilic synthetic polymer, such as polyvinylalcohol.

In another embodiment, the HGF variants are entrapped in microcapsules, prepared by, for instance, coacervations techniques or interfacial polymerization, in colloidal drug delivery systems (e.g. liposomes, albumin microspheres, microemusions, nano-particles and nanocapsules) or in macroemulsions. Such techniques are disclosed in *Remington's Pharmaceutical Sciences*, 16th Ed., MACK Pub. (1980), and are well-known to the skilled artisan.

Certain aspects of the invention are described in greater detail in the non-limiting examples that follow.

EXAMPLES

The protocols described below are referenced in Examples 1-8.

Cell Culture

Cells including the M426 human embryonic lung fibroblast (S. A. Aaronson and G. J. Todaro, *Virology* 36: 254-261 (1968), SK-LMS-1 human leiomyosarcoma (J. Fogh and G. Trempe In: *Human Tumor Cells In Vitro*, J. Fogh (ed.), Plenum Press, New York 115-159), and COS-1 monkey kidney epithelial (Gluzman et al., *Cell* 23: 175-182 (1981) cell lines were maintained in Dulbecco's modified Eagle's medium (DMEM) supplemented with 10% fetal calf serum (Bethesda Research Laboratories). B5/589 human mammary epithelial cells (M. R. Stampfer and J. C. Bartley, *Proc. Natl. Acad. Sci. U.S.A.* 82: 2394-2398 (1985) were grown as described (Rubin et al., *Proc. Natl. Acad. Sci. USA* 86: 802 (1989)) NIH/3T3 fibroblasts (Jainchill., *J. of Virol.* 4: 549-553 (1969)) were maintained in DMEM supplemented with 10% calf serum.

Mitogenic Assays

DNA synthesis was measured as previously described (Rubin., *Proc. Natl. Acad. Sci. USA* 86: 802 (1989)). Ninety-six well microtiter plates were precoated with human fibronectin at 1 µg/cm$^2$ prior to seeding with B5/589 cells. [$^3$H]-thymidine incorporation was determined during a 6-hr period beginning 16 hr after addition of samples. Trichloroacetic acid-insoluble DNA was collected and counted. HGF used in this study was purified in this laboratory as has been reported (Rubin et al., *Proc. Natl. Acad. Sci. USA* 88: 415 (1991)), and human recombinant EGF was purchased from Upstate Biotechnology Inc.

Immunoprecipitation

Cells in 100 mm tissue culture plates were labeled with 0.1 mCi/ml of [$^{35}$S]-methionine and cysteine (spec. act. 1150 Ci/ml; Du Pont-New England Nuclear) in 50 µg/ml of heparin for 4 hours as previously described (Rubin et al., *Proc. Natl. Acad. Sci. USA* 88: 415 (1991)). Conditioned medium was concentrated 20-fold in Centricon-10 microconcentrator (Amicon) and immunoprecipitated with nonimmune or HGF neutralizing antiserum. Immunoprecipitates were absorbed onto Gamma-bind G agarose (Genex) and washed three times with 10 mM Tris-HCl buffer containing 150 mM NaCl, 0.05% Tween-20, 0.1% SDS, 1% Np-40, 1 mM EDTA, and 10 mM KCl. Samples were analyzed under reducing (with 100 mM β-mercaptoethanol) and non-reducing conditions on 10%, 12.5% or 14% SDS-PAGE. Gels were fixed, treated with enlightening solution (New England Nuclear), dried, and exposed to Kodak AR film at −70° C.

Northern Analysis

Poly(A)$^+$RNA was isolated by oligo-dT columns as described (Maniatis et al., *Molecular cloning. A Laboratory Manual* Cold Spring Harbor, N.Y.: Cold Spring Harbor Laboratory (1982)). Following electrophoresis in 1% denaturing formaldehyde agarose gels, samples were transferred onto nitrocellulose filters (Maniatis et al., *Molecular cloning. A Laboratory Manual* (Cold Spring Harbor, N.Y.: Cold Spring Harbor Laboratory (1982)). Blots were hybridized to [$^{32}$P]-labeled randomly-primed DNA probes in 40% formamide, 6×SSC, 5×Denhardt's solution, 50 mM sodium phosphate (pH6.8), and 250 µg/ml of sonicated salmon sperm DNA at 42° C. for 12 hours. After hybridization, filters were washed twice in 1×SSC, 0.1% SDS at room temperature. The final wash was carried out in 0.1×SSC, 0.1% SDS at 55° C. Filters were dried and exposed to X-ray films for 5-8 days at −70° C. Hybridization probes were generated by PCR and purified on low-melting temperature agarose gels. The nucleotide sequence of each probe was numbered according to the HGF sequence of Miyazawa et al., *Biochem. Biophys. Res. Commun.* 163: 967-973 (1989) as follows:

| | |
|---|---|
| H/L (heavy and light chains) | −24 to +2187 |
| H (heavy chain) | +189 to +1143 |
| L (light chain) | +1475 to 2122 | cDNA Cloning and Sequencing

Approximately 1×10$^6$ phage plaques from an M426 cDNA library, see Finch et al., *Science* 245: 752-755 (1989), were plated, and duplicate filters were hybridized separately to radiolabeled probes H and L (see above) under conditions identical to those described for Northern analysis. Restriction mapping of plaque purified positive clones was performed using standard procedures (Maniatis et al., *Molecular cloning. A Laboratory Manual* (Cold Spring Harbor, N.Y.: Cold Spring Harbor Laboratory (1982)). cDNA inserts were excised and subcloned into the M13mp18 vector for sequencing analysis by the dideoxy chain-termination method. (Sanger et al., *J. Mol. Biol.* 143: 161-178 (1977).

PCR Analysis

For PCR of mRNA, 1 µg of poly(A)$_+$ RNA was first reverse-transcribed by avian myeloblastosis virus (AMC) reverse transcriptase (Bethesda Research Laboratories) using random hexamers (Pharmacia) as primers (Noonan et al., *Nucleic Acids Res.* 16: 10366 (1988)). Eight percent (~80ng) of the first-strand cDNA products were used directly in PCR (Saiki et al., *Science* 230: 1350-1354 (1985)). For routine PCR, 80 ng of cDNA were subjected to 30 cycles of amplification using primers P1 and P2 (see FIG. 4). Cycling conditions were: 1 minute at 94° C., 2 minutes at 60° C., and 3 minutes at 72° C. Aliquots (10%) of each reaction mixture were analyzed on 3% agarose gel. For PCR cloning of genomic DNA, PCR was carried out with BamHI linker-primers P1B and P2B (FIG. 4) and amplified DNA fragments were digested with BamHI. The resultant BamHI fragments were purified on low-melting temperature agarose gel and subcloned into the M13mp18 vector for sequencing analysis.

Transient Expression in COS-1 Cells

The HGF/NK2 coding sequence was generated by PCR using BamHI linker-primers, P3 and P4 (FIG. 4) and subcloned into the BamHI site of the vector pCDV-1 (Okayama et al., *Mol. Cell. Biol.* 3: 280-289 (1983)) in both orientations. The HGF/NK2 cDNA insert in a selected construct was sequenced to ensure that the PCR product was correct. Similar techniques were employed to subclone the HGF/NK1 cDNA sequence into vectors for recombinant expression. Ten µg (unless otherwise stated) of each plasmid DNA was transfected by the calcium phosphate precipitation method (Wigler et al., *Cell* 11: 223-232 (1977)) into COS-1 cells (Y. Gluzman, *Cell* 23: 175-182 (1981)). At 48 hours, proteins in conditioned medium were processed for labeling, immunoprecipitation and 10% SDS-PAGE under reducing and non-reducing conditions as described above.

Protein Purification

A. HGF/NK2

Six liters of conditioned medium from SK-LMS-1 cells grown in 175-cm$^2$ T flasks were prefiltered through a 0.5-µm filter (Millipore HAWP 142 50), and concentrated to 300 ml by a Pellicon cassette system having a 10 kD molecular mass cutoff (Millipore PTGC 000 05). Concentrated medium was loaded into heparin-Sepharose resin (4 ml. bed volume, LXB/Pharmacia) that had been equilibrated in 20 mM Tris-HC-1, pH7.5/0.3 M NaCL. The sample was eluted with a modified linear gradient of increasing NaCl concentration. Aliquots from each fraction were subjected to immunoblot analysis with antiserum raised against HGF (final dilution 1:500) to identify the presence of HGF/NK2. Pooled fractions were further resolved on a TSK G3000 sizing column (LKB/Pharmacia) in 20 mM Tris-HCl, pH6.8/1.0 M NaCl. The purity and identity of the HGF/NK2 protein were determined by silver-stain analysis (Merril et al., *Science* 211: 1437-1438 (1981)) and immunoblotting under reducing and non-reducing conditions. Fractions containing >95% of HGF/NK2 were selected for biological analysis. Protein concentration was estimated by optical density, assuming $A_{1\%\ 214}$=140.

B. HGF/NK1

One to five liters of conditioned medium from HGF/NK1 NIH/3T3 transfectants were concentrated in a Amicon ultrafiltration device with a membrane having a 10 kD molecular weight cutoff. The concentrated medium (~100 ml) was applied to heparin-Sepharose resin as described for HGF/NK2, and eluted by stepwise increments in NaCl concentration. HGF/NK1 was recovered in fractions eluted with 0.8M NaCl. This material was further purified by sizing chromatography with either a TSK G2000 or Supradex 75 column (both from LKB/Pharmacia), in a neutral, buffered hypertonic solution such as 20 mM Tris-HCl, pH 6.8/1.0 M NaCl. In some instances, HGF/NK1-containing fractions from either the heparin-Sepharose or sizing columns were concentrated in Centricon-10 devices and further purified by reverse-phase HPLC on a C4 column. The conditions for this chromatography were as previously described for HGF (Rubin et al., *Proc. Natl. Acad. Sci. USA* 88: 415-419 (1991)). Throughout this work, HGF/NK1 was monitored by immunoblot analysis with HGF antiserum.

Affinity Cross-linking

TSK-purified HGF/NK2 was iodinated by the chloramine-T method (W. M. Hunter and F. C. Greenwood, *Nature* 194: 495-496 (1962)) and represented over 99% of the labeled material in the preparation as determined by SDS-PAGE analysis. Affinity cross-linking experiments were performed on 6-well plates seeded with B5/589 cells at a density of $5\times10^5$ per well. To each well, HGF/NK2 ($5\times10^5$ cpm at a specific activity of ~200 µCi/µg) was added with or without cold competitors in HEPES binding buffer (100 mM HEPES, 150 mM KCl, 1.2 mM $MgSO_4$, 8.8 mM dextrose, 2 µg/ml heparin, and 0.1% BSA, pH7.4). Following incubation at room temperature for 45 minutes, cells were washed twice in cold HEPES saline (pH 7.4). Disuccinimidyl suberate (Pierce) in dimethyl sulfoxide was added to a final concentration of 250 µM and incubated for 15 min. Samples were then quenched with 100 µl of 20 mM Tris /100 mM glycine/1 mM EDTA for 1 minute and rinsed in HEPES saline. Cells were extracted with Laemmli sample buffer and resolved on 6.5% SDS-PAGE under reducing conditions.

Example 1

Figure 1:
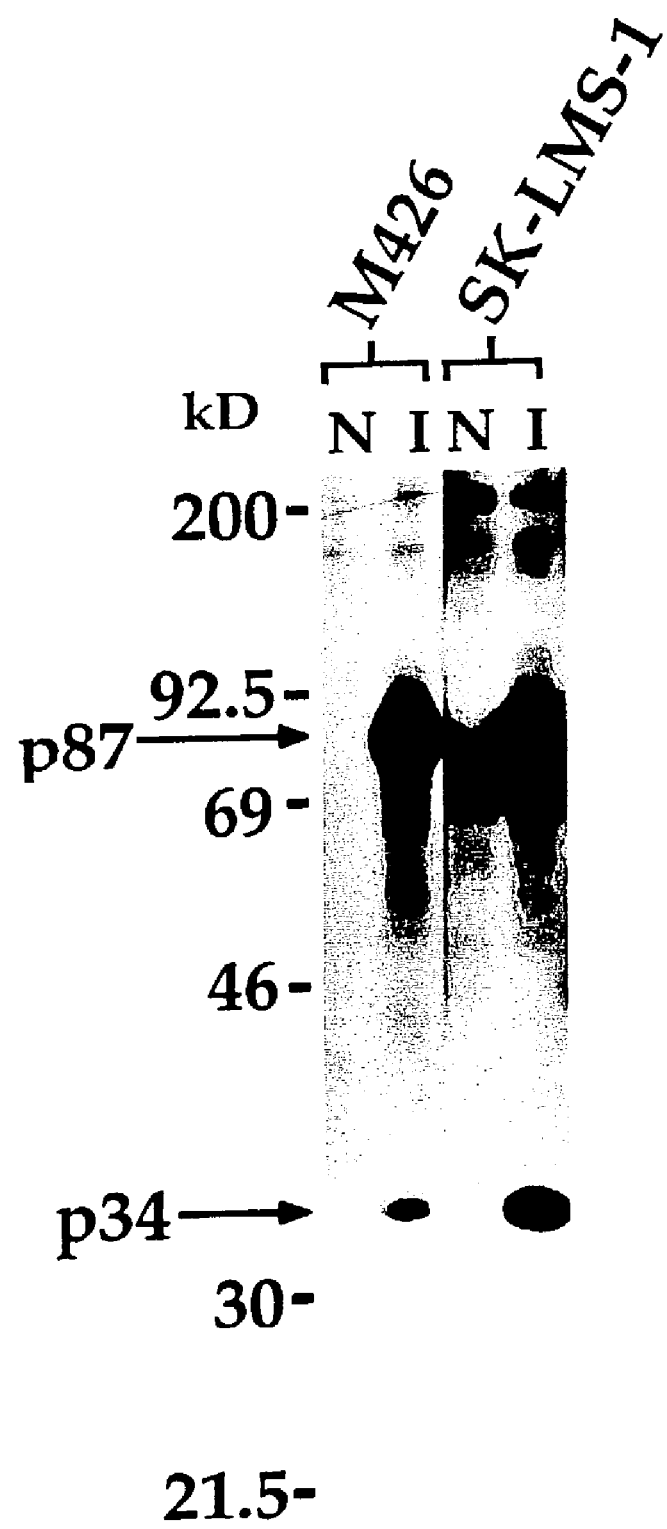
FIG. 1 shows the detection of p34 (HGF/NK2) in M426 and SK-LMS-1 cells. Equivalent amounts of [$^{35}$S]-methionine and cysteine labeled conditioned medium from M426 and SK-LMS-1 cells were immunoprecipitated with non-immune (N) and HGF immune-serum (I). Proteins were subjected to 10% SDS-PAGE under non-reducing conditions. HGFp87 and p34 are indicated by arrows, and molecular weight markers are shown in kD.

Detection of a Small Naturally Occurring HGF Immunoreactive Species and its Putative Transcript Previous studies demonstrated that HGF is synthesized as a single-chain polypeptide with an apparent molecular mass (Mr) of 87,000 (87 kD). It can be cleaved into a heterodimeric form consisting of a heavy- ($M_r$ 60 kD) and light-chain ($M_r$~30 kD) held together by disulfide bonds. Neutralizing antiserum against purified HGF was used to immunoprecipitate proteins in conditioned medium from metabolically labeled M426 human embryonic lung fibroblasts. When sodium dodecyl sulfate polyacrylamide gel electrophoresis (SDS-PAGE) was performed under reducing conditions, the single-chain form (HGFp87) was the predominant species. While there was no evidence of the processed heavy- and light-chains, low levels of a HGF immunoreactive molecule of $M_r$ ~34 kD (p34) were observed (FIG. 1). Pulse chase experiments showed that both HGFp87 and p34 shared similar kinetics of synthesis and secretion arguing against the likelihood that p34 was a HGFp87 degradation product. When the same experiment was performed with another HGF-producer, a leiomyosarcoma cell line (SK-LMS-1), a similar pattern was seen except that p34 was relatively more abundant (FIG. 1).

Figure 2:
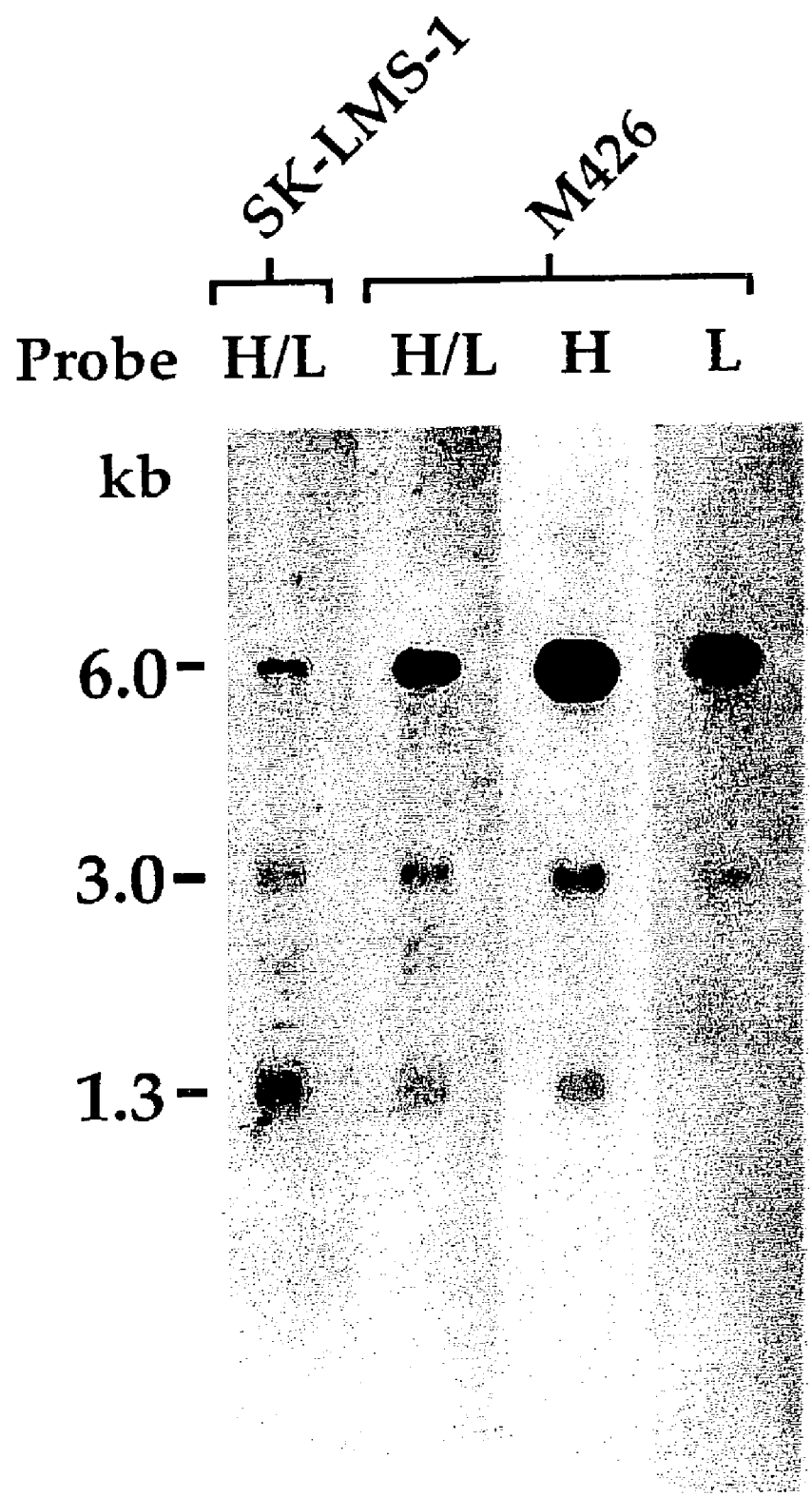
FIG. 2 depicts the Northern analysis of RNA from M426 and SK-LMS-1 cells. Two μg of poly(A)$^+$ RNA from SK-LMS-1 and M426 cells were electrophoresed on 1% agarose gels, and Northern blots were hybridized with either HGF coding region (H/L), heavy (H) or light (L) chain probes. The sizes in kilobases (kb) of three major HGF-related transcripts are indicated.

To gain further understanding of the relationship between HGFp87 and p34, poly(A)$^+$ RNA was prepared from M426 and SK-LMS-1 cells and subjected to Northern blot analysis using the full-length HGF coding sequence as probe. As shown in FIG. 2, two major transcripts of 6.0 and 3.0 kilobases (kb) were detected in both lines. Each of these transcripts has previously been shown to encode the full-length growth factor (Rubin et al., *Proc. Natl. Acad. Sci. USA* 88: 415 (1991). A third HGF hybridizing RNA of ~1.3 kb was present at a relatively low level in M426 cells, but was expressed at higher levels in SK-LMS-I cells. This pattern was consistent with the relative levels of p34 observed in the two cell lines, suggesting that p34 might be encoded by the novel 1.3 kb transcript. Based on the fact that the complete HGF coding sequence is ~2.0 kb, the 1.3 kb transcript could only represent a portion of this region. To test this, the same Northern blot was hybridized separately with probes derived from either the N-terminal heavy-chain or the C-terminal light-chain. Whereas both probes were able to detect the 6.0 and 3.0 kb transcripts, only the heavy-chain probe was capable of recognizing the 1.3 kb message (FIG. 2). These results suggested that this RNA species encoded a truncated version of the HGF molecule containing sequences from its N-terminal region.

Other faint bands were also detected in the Northern blots hybridized with probes derived from HGF (FIG. 2), including one at approximately 2.2 kb. The significance of this observation became apparent after further study detailed in Example 2, below.

Example 2

Isolation of HGF cDNA Clones Encoding Only the N-terminal and First One or Two Kringle Domains In an attempt to isolate cDNA clones corresponding to the 1.3 kb transcript, an M426 cDNA library was differentially screened with both HGF heavy- and light-chain probes. Clones that specifically hybridized to the heavy-but not the light-chain probe were plaque purified. Based on the sizes and physical maps of the inserts, one cDNA clone, pH45 with an insert of ~1.2 kb was selected for sequencing. As shown schematically in FIG. 4A, clone pH45 depicted a transcript of 1199 basepairs (bp) composed of a short 5'-untranslated region of 75 bp, an open reading frame of 870 bp and a 254 bp 3'-untranslated region containing a polyadenylation signal, AATAAA. The open reading frame predicted a 290 amino acid truncated version of HGF consisting of a signal peptide, an N-terminal domain (N), and the first two kringle domains (K1 and K2) with a calculated Mr of ~30 kD excluding the signal peptide. This sequence, which is designated NK2 was identical to that of HGF cDNA until it diverged at a point which coincided precisely with the end of the K2 domain. The NK2 open reading frame continued for two additional amino acids followed by an in-frame stop codon (TAA) (FIGS. 3 and 4A).

To ascertain the authenticity of the cDNA clone, polymerase chain reaction (PCR) analysis was performed with primers P1 and P2 (FIG. 4A), the latter of which was specific for the HGF/NK2 transcript. FIG. 4B shows the existence of the predicted 220 bp PCR fragment in RNA of M426 and SK-LMS-1 cells but not in B5/589 cells, which lack detectable HGF transcripts. The gene structure of this region was further analyzed by amplifying the corresponding genomic sequence using the same PCR primers (FIG. 4B). Sequencing of the PCR product revealed a .about.400 bp intron with the consensus splice donor/acceptor sequences CG/GT and AG/AG at the intron-exon boundaries, which aligned precisely with the predicted splice junction in the NK2 cDNA clone (SEQ ID NO: 13) (FIG. 4A). Thus, the 1.3 kb NK2 transcript is likely generated during precursor RNA processing by joining of the K2 exon to an alternative exon containing a termination codon instead of the K3 exon.

By means of differential screening strategy described above, three additional cDNA clones that specifically hybridized to the HGF heavy chain probe, as opposed to the light chain probe, were isolated from the M426 library. One of these was about 1.6 kb and contained the coding sequence for HGF/NK2; it differed from the 1.3 kb insert only insofar as it included a longer stretch of 3' untranslated sequence. However, the other two inserts, one 1.7 and the other 2.2 kb, encoded the N-terminal and first kringle domain; they differed from each other in the terminal portion of their coding sequence (involving a few amino acid residues after the kringle domain) and in their 3' untranslated regions. The coding sequences of these NK1 cDNAs are presented in FIGS. 9 (as shown in SEQ ID NO: 9) and 10 (as shown in SEQ ID NO: 11), respectively.

As noted above, a close examination of the HGF hybridization pattern in Northern blot analysis revealed a weak 2.2 kb band as well as a diffuse signal at 1.3-1.7 kb (FIG. 2) which probably represent the transcripts corresponding to these low abundance cDNAs. When polyA+ RNA from M426 cells was hybridized with a probe corresponding to a portion of the 3'-untranslated sequence of the 2.2 kb cDNA encoding HGF/NK1, a 2.2 kb transcript was detected and matched a faint band observed with a probe to the heavy chain region (FIGS. 2 and 11). This indicated that HGF/NK1 is encoded by a bona fide, naturally occurring transcript.

Example 3

Recombinant Expression of HGF/NK2 cDNA Identifies its Product as the Small HGF Crossreactive Species In order to test whether the NK2 transcript encodes the p34 protein detected in M426 and SK-LMS-1 cells, the NK2 coding region was subcloned into the expression vector, pCDV-1, in both anti-sense (pC45as) and sense (pC45s) orientations. Conditioned medium of COS-1 cells transfected with either construct was collected and immunoprecipitated with HGF neutralizing antibodies followed by SDS-PAGE analysis. As shown in FIG. 5A, pC45s transfected COS-1 cells secreted a 34 kD HGF immunoreactive recombinant protein (rHGF/NK2) not detected when COS-1 cells were transfected with the pC45as construct. The size of this protein corresponded closely to that of p34 from M426 and SK-LMS-1 cells (FIG. 5A). When the same experiment was performed under non-reducing conditions, the mobility of both recombinant and naturally occurring p34 shifted to an apparent Mr of ~28 kD (FIG. 5B), providing further evidence that p34 and rHGF/NK2 were structurally indistinguishable.

The next experiment compared the heparin-binding properties of p34 and rHGF/NK2. Conditioned medium collected from SK-LMS-1 and pC45s-transfected COS-1 cells were each applied to heparin-Sepharose resin, and bound proteins were eluted which indicated that the p34 protein secreted by M426 and SK-LMS-1 cells represented a truncated version of HGF expressed from the NK2 transcript. Thus, the p34 protein was designated as HGF/NK2.

The HGF/NK2 coding region also was subcloned into the pZIPneo expression vector and subsequently transfected into NIH/3T3 mouse fibroblasts. The metabolically labeled protein was detected in the conditioned medium of transfected cells, but levels were not sufficient for preparative work.

Example 4

Detection of HGF/NK1 Protein in a Transient, Recombinant Expression System

When the HGF/NK1 coding sequence was transiently expressed in $^{35}$S-labeled COS-1 cells, a small protein was specifically immunoprecipitated with antiserum raised against full-length HGF. The protein had an apparent size of ~20 kD under non-reducing and ~23 kD under reducing conditions, and matched the electrophoretic behavior of a protein similarly immunoprecipitated from metabolically labeled SK-LMS-1 cells (FIG. 12). The size of this protein was consistent with HGF/NK1, based on the coding sequence. The fact that it was immunoprecipitated with the HGF antiserum indicated that this reagent could be used to detect HGF/NK1 protein during purification of the protein.

Example 5

Purified HGF/NK2 is a Specific Inhibitor of HGF Mitogenic Activity

To investigate its biological activity, HGF/NK2 was purified from culture fluids of SK-LMS-1 cells by a three-step procedure combining ultrafiltration, heparin-Sepharose and TSK sieving chromatography. The purified protein exhibited the characteristic mobility shift under non-reducing and reducing conditions and was immunoreactive with anti-HGF serum, thereby confirming its identity as HGF/NK2 (FIG. 6).

To test the mitogenic activity of HGF/NK2, a human mammary epithelial cell line, B5/589, was used as the target cell. While HGF stimulated [$^3$H]-thymidine incorporation with a half-maximal effect at ~0.25 nM, under identical conditions HGF/NK2 at concentrations as high as 10 nM caused no enhancement concentrations, a dose-dependent inhibition of [$^3$H]-thymidine incorporation was observed (FIG. 7B). To achieve a 50% inhibition, a 10- to 20-fold molar excess of HGF/NK2 over HGF was required. Similar results were obtained when human melanocytes were used as target cells. Moveover, the inhibition was specific for HGF since HGF/NK2 did not impair the mitogenic activity of epidermal growth factor (EGF) (FIG. 7B). Similarly, HGF/NK1 also specifically inhibited the mitogenic activity of HGF.

Example 6

Purification of HGF/NK1 Protein from the Conditioned Medium of NIH/3T3 Transfectants NIH/3T3 cells were transfected with a vector containing the HGF/NK1 coding sequence to generate a stable, recombinant source of HGF/NK1 protein. Immunoblot analysis with the HGF antiserum confirmed that HGF/NK1 was secreted by transfected cells into their culture fluid. The protein was enriched by binding to heparin sepharose and eluted in solvent containing 0.8M NaCl. Further purification was achieved with sizing chromatography and/or reverse-phase HPLC. Silver-stain and immunoblot analysis identified the HGF/NK1 in the purified fractions.

Example 7

Competitive Binding of HGF/NK2 and HGF to the HGF Receptor

It was recently demonstrated that the c-met protooncogene product, a membrane-spanning tyrosine kinase, is the cell surface receptor for HGF (Bottaro et al., Science 251: 802 (1991)). To elucidate the mechanism by which HGF/NK2 acted as an antagonist of HGF mitogenic activity, cross-linking studies of [$^{125}$I]-HGF/NK2 to B5/589 cells were performed. As shown in FIG. 8, a single major cross-linked species of 170 kD was detected under reducing conditions. This band corresponds to the 145 kD B-subunit of the processed c-met product cross-linked to HGF/NK2 (Bottaro et al., Science 251: 802 (1991)). Increasing concentrations of either unlabeled HGF/NK2 or HGF effectively competed with the labeled ligand in the cross-linking reaction. On a molar basis, HGF was estimated to be 3 to 5 times more effective than HGF/NK2 itself as a competitor of [$^{125}$I]-HGF/NK2 cross-linking. Under the same conditions, EGF failed to block HGF/NK2 cross-linking (FIG. 8). All of these findings demonstrate specific competitive binding of HGF/NK2 and HGF to the same cell surface receptor molecule.

Example 8

Coexpression of Human HGF/NK2 with Human Met does not Induce Cell Transformation in Contrast to HGF The lack of HGF/NK2 growth promoting activity was also demonstrated in co-transfection experiments in which a construct encoding either of these ligands was introduced into NIH/3T3 cells simultaneously transfected with a vector containing the human c-met coding sequence. In contrast to human HGF/human Met co-transfectants which were characterized by a significant number of transformed foci, the HGF/NK2/Met co-transfectants failed to show evidence of cell transformation. This different outcome could not be attributed to an absence of HGF/NK2 expression or variation in the degree of Met expression in the co-transfectants, judging from immunological analysis. Expression of human Met itself also was not transforming. Thus, these results indicated that HGF/NK2 did not behave like HGF in transfection bioassays. To the extent that cell transformation reflects promotion of cell growth, the data indicate that HGF/NK2 is devoid of such stimulatory activity.

Example 9

Prokaryotic Expression of NK1 and NK2

Materials and Methods

Construction of expression plasmids. HGF/NK1 and HGF/NK2, products of alternately spliced transcripts of HGF (Chan et al., Science, 254: 1382 (1990)), were produced in E. coli using the T7 expression system developed by Studier et al., Meth. Enzym. 185: 60-89 (1990). The DNA encoding the desired polypeptides was generated as an NdeI-BamHI fragment using the polymerase chain reaction as previously described (Scharf et al., Science 230: 1076-1078 (1986), and cloned into pET11a (Studier et al, supra).

The construct pET11-HGF/N encodes the polypeptide: $MG_{31} Q_{32} R_{33} \ldots R_{126} N_{127OH}$. The construct pET11-HGF/NK1 encodes the polypeptide: $MG_{31} Q_{32} R_{33} \ldots S_{207} E_{208} GK_{OH}$. pET11-HGF/NK2 encodes the polypeptide: $MG_{31} Q_{32} R_{33} \ldots T_{287} C_{288}ET_{OH}$. The amino numbering corresponds to that of full length HGF (Rubin et al., PNAS USA 88: 415-419 (1991). pET11-HGF/NK2 (C214A) was derived from pET11-HGF/NK2 using the polymerase chain reaction to change the coding for cysteine-214 to one encoding alanine (Higuchi, et al., Nucl. Acid. Res. 16: 7351-7367 (1988). The DNA sequences of all HGF coding regions were verified using an Applied Biosystems 373A DNA sequencer using procedures and reagents supplied by the manufacturer.

Expression of HGF/N, HGF/NK1 and HGF/NK2 in E. coli. Plasmid DNAs were transformed into E. coli strain BL21 (DE3) (Studier, et al., supra). Fermentations were in a MD2 2-1 benchtop fermentor in the following medium: 2% glucose, 2% Bacto tryptone, 1% yeast extract, 0.5% sodium citrate, 1% dibasic potassium phosphate, 10 mM magnesium sulfate, 200 mg/l ampicillin and trace metals. Cells were grown at 37° C. and 30% p0$_2$ (equivalent to an aeration rate of 2-1 min$^{-1}$). When the cell density reached an optical density of 10.0 at 600 nm, protein expression was induced with 2 mM IPTG for 3.5 h. The fermentations yielded about 50 g wet weight of cells which were stored at −80° C. until required.

Protein Purification. The following procedure was used for all proteins (HGF/N, HGF/NKI, HGF/NK2 and HGF/NK2 C184A). Cells (~50 g wet weight) were resuspended into 200 ml of 100 mM Tris-HCl, pH 8.0, containing 5 mM EDTA and 5 mM benzamidine-HCl (break buffer) and passed once through a French pressure cell (SLM-Aminco) operated at 18,000 psi. The suspension was briefly sonicated, Triton X-100 was added (0.1%), then centrifuged at 10,000 g for 45 min. The pellet was resuspended into 250 ml of break buffer and recentrifuged. The washed pellet was solubilized with 35-40 ml of 50 mM Tris-HCl, pH 8, containing 8M guanidine-HCl(Gdn-HCl) and 100 mM dithiothreitol. The slightly cloudy solution was clarified by centrifugation at 100,000 g for 30 min and applied at 5 ml min$^{-1}$ to a column 6.0 cm diameter×60 cm of Superdex S-200 (Pharmacia) equilibrated with 50 mM Tris-HCl, pH 8.0, containing 4 M Gdn-HCl and 10 mM DTT. The column was eluted at 5-ml min$^{-1}$ and 20-ml fractions were collected. Fractions were analyzed by SDS-PAGE after removal of the Gdn-HCl using the method of Pepinsky, Anal. Biochem. 195: 177-181 (1990) (1990). Selected fractions containing HGF proteins were pooled and stored at −80° C. Pooled protein was acidified by the addition of 5% acetic acid, and applied in 20 ml batches to a column 2.5 cm×10 cm of Poros R2 (PerSeptive Biosystems) equilibrated in 0.1% TFA. The column was eluted with a gradient of acetonitrile in 0.1% TFA. The main protein peak was pooled and lyophilized.

Protein folding. Lyophilized protein was dissolved with 8M Gdn-HCl containing 20 mM dithiothreitol to give a solution: 30-40 mg ml$^{-1}$. The protein solution (~100 mgs) was slowly diluted at 20° C. to about 0.1 mg/ml in 1-liter of the following refolding buffer: 100 mM Tris-HCl, pH 7.3, containing 2.5 M urea, 5 mM oxidized glutathione and 1 mM reduced glutathione. The solution was incubated at 4° C. for 24 hours then transferred to dialysis tubing and dialyzed for 12-h against 5-1 of 50 mM Tris-HCl, pH 7.3, containing 100 mM NaCl. The dialysis was continued for at least 12 hours against 20-1 of the same buffer with two changes of buffer. All dialysis stages were performed at 4° C. The proteins were concentrated by ultrafiltration to about 50 ml using an Amicon Model 2000 stirred cell (total capacity 2-1) with a Diaflo PM-10 membrane (Amicon), clarified by filtration or centrifugation, then concentrated further to 5-6 ml using either Centriprep-10 centrifuge concentrators (Amicon) or a 200-ml ultrafiltarion stirred cell with a PM-10 membrane. The concentrate was applied to a Superdex S-75 column 2.6 cm diameter×60 cm (Pharmacia) equilibrated in 50 mM Tris-HCl, pH 7.5, containing 100 mM NaCl. The column was eluted at 1 ml min$^{-1}$ and 4 ml fractions were collected. Fractions containing correctly folded protein were pooled. Proteins were concentrated to 1 mg ml$^{-1}$ or higher, using Centriprep-10 units (Amicon), then sterile filtered with Millex GV 0.22-μ, filter units (Millipore) and stored at −80° C.

Determination of protein concentration. The protein concentration of purified proteins were determined by measuring absorbencies at 280 nm in a 1-cm pathlength cell using a double-beam, diode array Hewlett-Packard 8450A UV/VIS spectrophotometer. The molar absorbance coefficients (ϵ) of native proteins were calculated from the amino acid compositions according to Wetlaufer (1960) and values of 8.34 mM$^{-1}$ cm$^{-1}$ (A$^{0.1\%}$=0.76); 25.77 mM$^{-1}$cm$^{-1}$ (A$^{0.1\%}$=1.25) and 49.93 mM$^{-1}$ cm$^{-1}$ (A$^{0.1\%}$=1.65) were used for HGF/N, HGF/NK1 and HGF/NK2, respectively.

Mass Spectroscopy Samples (0.3-0.5 mg/ml) were dialysed or gel filtrated into 5% acetic acid. The solutions were diluted to about 15-20 μM and 25 μl of this mixed with 25 μl of hexafluoroisopropanol in preparation for electrospray mass spectroscopy (MS). The protein solutions were infused at a rate of 0.5 μl/min into an Analytica electrospray source fitted to a Jeol JMS-SX102 mass spectrometer operated at 5 kV accelerating voltage. The electrospray instrument was calibrated against lysozyme, and molecular weights of the measured proteins were obtained by deconvolution of the resultant mass/charge peak distributions. By this method the determined mass accuracy was better than 0.01%.

Analytical ultracentrifugation. Analytical ultracentrifugation was carried out using a Beckman Optima XL-A analytical ultracentrifuge with an An-60Ti rotor and standard double-sector centerpiece cells. For equilibrium measurements, centrifugations (14-20 hours at 20° C.) were at 25,000, 23,000 and 18,000 rpm for HGF/N; HGF/NK1 and HGF/NK2, respectively. Sedimentation velocity measurements were made at 45,000 rpm for 2-3 hours at 20° C. with data collection every 15 min. Data was analyzed using both the standard Beckman XL-A data analysis software (v3.0 for DOS) and the Beckman-Origin software (v2.0 for Windows). Protein partial specific volumes were calculated from amino acid compositions (Cohn and Edsall, *Proteins, Amino Acids & Peptides*, pp 370, Van Nostrand-Reinhold, Princeton, (1943)).

Values of 0.735; 0.727 and 0.719 g ml$^{-1}$ were used for HGF/N; HGF/NK1 and NK2, respectively. Solvent densities were either calculated as described by Laue et al., *Ultracentrif. in Biochem. and Polymer Sci.*, Harding et al., Eds. pp. 90-125, Royal Soc. for Chem., Cambridge, Eng. (1992) or the values were taken from the International Critical Tables (1929).

Circular dichroism. CD spectra were recorded on a Jasco J-720 spectropolarimeter. Measurements in the near (340-240 nm) and far (260-180 nm) ultraviolet regions were made using 1-cm and 0.02-cm pathlength cells respectively. A 1-nm bandwidth was used for both spectral regions. The protein solutions were about 0.75-1 mg ml$^{-1}$. Protein buffers were exchanged for 50 mM sodium phosphate, pH 7.5 using Sephadex G-25M (PD-10 column: Pharmacia). Immediately prior to use, solutions were filtered with Millex-GV 0.22-μm filter units (Millipore) and degassed. Secondary structures were estimated using the methods of Perczel et al., *Anal. Biochem.* 203: 83-93 (1992)).

Tissue Culture

B5/589 human mammary epithelial cells and Madin-Darby Canine Kidney (MDCK) cells were maintained as described previously (Rubin et al., *PNAS* 86: 802-806, (1989)).

Mitogenicity Assay

DNA synthesis was assayed by incorporation of [$^3$H]-thymidine into a trichloroacetic acid precipitable cell fraction as described previously (Rubin et al., *PNAS*, 86: 802 (1989)).

Scatter Assay

MDCK cell movement, observed as the dispersion or scatter of single cells from tightly grouped colonies, was assayed as described previously (Stoker and Perryman, *J. Cell Sci.* 77: 209-223, (1985)). Treatments are made over several serial dilutions, and cell scatter observed by light microscopy is expressed in arbitrary units from a minimum of 1 (groups of cells and few single cells) to a maximum of 4 (all single cells).

HGF Receptor Phosphorylation

B5/589 mammary epithelial cells grown to confluence in 15 cm dishes were serum-deprived for 16 h, then treated with each HGF isoform at the concentration indicated, or left untreated, and incubated for 10 min at 37° C. The cell culture medium was then aspirated, Triton X-100 extracts were prepared and phosphotyrosyl proteins were immunoprecipitated using monoclonal antiphosphotyrosine antibodies (anti-p Y; Upstate Biotechnology, Inc.). Anti-pY immunoprecipitates were subjected to SDS-PAGE, transferred to PVDF membranes, and immunoblotted using antisera to c-met (Santa Cruz Biotechnology, Inc.) and [$^{125}$I]-protein-A. The amount of anti-pY-precipitable HGF receptor was quantitated by autoradiography using a PhosphorImager (Molecular Dynamics, Inc.).

Ligand/Receptor Covalent Affinity Crosslinking

[$^{125}$I]-HGF/NK2 was prepared as described previously (Bottaro et al., *Science*, 251: 802-804 (1991)). [$^{125}$I]-HGF/NK2, in the presence and absence of excess unlabeled HGF isoforms, was crosslinked to HGF receptors on B5/589 cells and observed by SDS-PAGE and autoradiography as described previously (Bottaro et al., supra). The relative affinities of HGF isoforms for interaction with HGF receptors was estimated based on their ability to displace [$^{125}$I]-HGF/NK2 from the 170 kDa crosslinked complex.

Example 10

HGF/NK1 is a Naturally Occurring HGF/SF Variant With Partial Agonist/Antagonist Activity Analysis of HGF/NK1 demonstrates that it retains the avid heparin-binding properties of HGF/SF, interacts with Met and behaves as a partial agonist/antagonist of HGF/SF growth-promoting activity.

Isolation and Analysis of HGF/NK1 cDNA Clones

An M426 cDNA library (Finch et al., *Science* (1989)) was differentially screened with probes corresponding to either the heavy or light chain regions of HGF/SF, as previously described (Chan et al., *Science* (1991)). Clones that specifically hybridized to the heavy chain probe were plaque purified. Distinct inserts were identified based on differences in size and physical maps defined by restriction enzymes PstI, XbaI and EcoRV (New England Biolabs, Inc.). Inserts pH46 and pH50 differed from each other and inserts such as pH45 which encoded HGF/NK2, and therefore were selected for sequencing. The sequences for HGF/NK1 encoded by pH46 and pH50 described herein have been deposited in GenBank (accession numbers PTA-894 and PTA-895 respectively).

Detection of HGF/NK1 Transcript

Poly (A)+RNA was isolated from M426 cells as described. Replicate samples (2 μg, each) were electrophoresed in a 1% denaturing formaldehyde agarose gel and transferred to nitrocellulose filters. The filers were prehybridized for 2 hours at 42° C. in Hybrisol (Oncor; 40% formamide, 10% dextran sulfate, 1% SDS, 6×SSC and blocking agents), and then hybridized for 15 hours in the same solution with [$^{32}$P]dCTP-labeled randomly primed probes corresponding either to the heavy or light chain of HGF/SF (Chan, et al. supra), or to a ~600 bp segment of the 3'-untranslated region of pH46 (generated by PCR using primers:). Filters were washed twice (30 min, each) in 2×SSC, 0.1% SDS at room temperature and twice (30 min, each) in 0.1×SSC, 0.1% SDS at 50° C. Filters were dried and exposed to Kodak XOMAT AR film for 24 hours.

Recombinant Expression and Purification of HGF/NK1 in NIH/3T3 Cells

The HGF/NK1 coding region from pH46 was generated by PCR using Bam H1 site-tagged oligonucleotide primers, and subcloned into the MMTneo vector (LaRochelle, *Science*). The resulting plasmid was transfected into 1.5×10$^5$ NIH/3T3 cells using 5 μg DNA and standard calcium phosphate precipitation methodology. Transfectants were selected in Geneticin (750 μg/ml) and expanded in 175 cm$^2$ T flasks for preparative work. Following 36 hours exposure to ZnCl$_2$, conditioned medium was collected, clarified by centrifugation (1000×g for 20 min, 4° C.) and concentrated 25-fold by ultrafiltration with a YM membrane (10 kDa cutoff, Amicon). HGF/NK1 was recovered from heparin-Sepharose resin (Pharmacia/LKB) essentially as described for HGF/SF (Rubin, supra, (1991)). Fractions containing HGF/NK1 as determined by immunoblotting (see below) were pooled, concentrated in Centriprep and/or Centricon devices (both from Amicon) and chromatographed on a TSK G2000 column (Pharmacia/LKB) equilibrated in 20 mM Tris-HCl (pH6.8), 1.0M NaCl. In some instances, material from heparin-Sepharose or TSK G2000 chromatography was purified by C4RP-HPLC as previously described for HGF/SF (Rubin, supra, (1991).

Recombinant Expression and Purification of HGF/NK1 in Baculovirus System

The HGF/NK1 coding sequence (from pH 46) tagged with Bam H1 restriction sites was subcloned into the Bam H1 site of the baculovirus vector pVL941 (Pharmingen, Calif.). Recombinant baculovirus was produced by cotransfecting Sf9 (*Spodoptera frugiperda*) insect cells with HGF/NK1-pVL941 and AcNPV (*Autographa californica*) baculovirus DNA by the calcium phosphate method as suggested by the manufacturer (BaculoGold transfection kit; Pharmingen, Calif.). Similarly, viral plaque purification, amplification, stock production and infections were performed according to protocols provided by the manufacturer.

For production of HGF/NK1 protein, 2×10$^8$ Sf9 cells were seeded in a 175 cm2 T flask containing Sf 900 medium (GIBCO-BRL) plus 10% fetal bovine serum. After a 1 hours incubation to facilitate cell attachment, the medium was replaced with fresh medium containing recombinant virus at a multiplicity of infection (MOI) of 10:1. One hours later, the culture was aspirated and fresh medium added. After 3 days, conditioned medium was harvested and either frozen at −20° C. or directly loaded onto a heparin-Poros HPLC column (2.7 ml bed volume; Perseptive Biosystems) at a flow rate of 5/ml/min. After washing the column with 20 mM phosphate buffer pH 7.4/0.3 M NaCl, protein was eluted with a linear gradient from 0.3-1.5 M NaCl. Fractions containing HGF/NK1, which eluted with 0.9-1.0 M NaCl, were identified by immunoblotting (see below) with a rabbit polyclonal antiserum raised against naturally occurring HGF/SF (Rubin et al., *PNAS* 1991).

Recombinant Expression and Purification of HGF/SF

The full-length coding region of HGF/SF was generated by PCR using Bam H1 restriction enzyme-tagged oligonucleotide primers and subcloned into the Bam H1 site of the baculovirus vector pVL941 which had been prepared as described (Luckow et al., *Virology* 170: 31 (1989)). Recombinant baculovirus was produced by introducing AcNPV DNA (1 μg) and HGF/SF-pVL (2 μg) simultaneously into Sf9 cells (American Type Culture Collection) by standard calcium phosphate transfection methodology. Sf9 cells were grown in Sf 900 serum free growth medium. After four days, supernatant fluid was harvested and screened for homologous recombination by visual inspection and dot-blot hybridization using a 32P-labeled, nick-translated HGF/SF cDNA probe. Purified recombinant virus was obtained after three rounds of plaque purification.

To obtain recombinant HGF/SF protein, Sf9 cells were infected with recombinant HGF/SF virus at an MOI of 10; subsequently cultures and media were handled as described above for HGF/NK1. HGF/SF was purified with heparin affinity chromatography using either a heparin-TSK (Toyo-Haas) or heparin-Poros column as described for baculovirus-expressed HGF/NK1.

Physical Detection of HGF/NK1 and HGF/SF Proteins

For immunoblotting, proteins were resolved in 12.5% (HGF/NK1) or 10% (HGF/SF) polyacrylamide-SKS gels under reducing or non-reducing conditions and transferred to Immobilon (PVDF) filters (Millipore). Blocking and detection of proteins with diluted, GammaBind (Pharmacia)-purified antiserum to HGF/SF (Rubin, supra (1991)) were as previously described (Bottaro et al., J. Biol. Chem., (1990)).

Silver-staining of protein resolved by SDSpPAGE was performed with Silver Stain Plus (Biorad).

Biological Assays

DNA synthesis by B5/589 human mammary epithelial cells was measured by [$^3$H]-thymidine incorporation as described in Rubin et al., supra (1989). Epidermal growth factor (murine, recombinant) was from Collaborative Research.

The scattering assay was performed with a subclone of MDCK cells, kindly provided by Dr. Robert Furlong, according to published methods (Stoker and Perryman, supra, 1985).

Met Tyrosine Phosphorylation

Confluent B5/589 cells were serum-starved for 24 hours, exposed to HGF/SF or HGF/NK1 for 10 min at 370° C., and lysed in Hepes solubilizer buffer (a50 mM Hepes pH 7.4, 1% Triton X-100 (vol/vol), 100 mM NaF, 2.5 mM Na orthovanadate, 10 mM sodium pyrophosphate, 2 mM PMSF, 10 μg/ml aprotinin, 10 μg/ml leupeptin) and immunoprecipitated with monoclonal antibody 4G10 to pTyr (5 μg/ml; Upstate Biotechnology, Inc.). Immunoprecipitated proteins were resolved by 7.5% SDS-PAGE and immunoblotted with a rabbit polyclonal antibody to a synthetic peptide corresponding to the caraboxy-terminal 28 amino acid residues of human Met according to the manufacturer's instructions (Santa Cruz Biotechnology).

HGF/NK1 Radioiodination and Chemical Crosslinking to Met

Purified HGF/NK1 (2 μg) was radiolabeled with chloramine T as described for HGF/NK2 (Bottaro, et al., supra, 1991).

B5a/a589 cells were incubated with Hepes binding buffer (Bottaro et al., supra, 1990) containing 0.9 nM [$^{125}$I]-HGF/NK1 (2.5×10$^5$ cpm; specific activity ~10 uCi/μg) for 45 min at room temperature, washed with cold Hepes-buffered saline (pH 7.4) and treated with 100 uM Bis (Sulfosuccinimidyl) Suberate (BS3; Pierce) for 15 min at room temperature. In some experiments, varying concentrations of unlabeled HGF/NK1 or HGF/SF were included in the binding buffer with [$^{125}$I]-HGF/NK1.

Prior to immunoprecipitation, cells were lysed with Hepes solubilizer buffer and proteins immunoprecipitated with the above-mentioned antiserum to Met peptide (50 μg/ml) in the absence or presence of competing peptide (1 μg/ml). Immunoprecipitated proteins were pelleted with immobilized protein-G (GammaBind, Pharmacia) and eluted with Laemmli buffer. Following electrophoresis in 6% SDS-PAGE, gels were dry and exposed to Kodak XOMAT AR film. Alternatively, cells were solubilized directly in SDS, boiled for 3 min in the presence of 100 mM β-mercaptoethanol and lysates were electrophoresed for autoradiography as above.

Isolation of cDNA clones encoding HGF/NK1. Hybridization of several transcripts to HGF/SF cDNA probes raised the possibility that distinct isoforms were encoded by alternative transcripts. Differential screening of an M426 human fibroblast cDNA library with HGF/SF heavy vs. light chain probes led to the isolation of several clones which hybridized only to the heavy chain probe. Restriction enzyme analysis indicated that multiple sequences were encoded by the different clones. One pattern typified by a 1.2 kb insert (pH45) specified an open reading frame (ORF) extending from the amino-terminus of the full-length factor through the second kringle domain (HGF/NK2), as previously reported. However, two other clones, pH46 and pH50, contained inserts of 2.2 and 1.7 kb, respectively, and exhibited related restriction maps. Sequence analysis revealed that each encoded a truncated version of HGF/SF consisting of the signal peptide, NH2-terminal domain and the first kringle domain (K1). Their sequences were completely divergent downstream from K1, although both ORFs predicted only a few amino acids beyond K1. Using a 0.6 kb probe derived from the unique 3'-untranslated region, Northern blot analysis of RNA from M426 cells identified a 2.2 kb transcript to the pH46 insert. Similar experiments were not performed with a probe from the 3'-ut of pH50. A low level of expression of the transcript corresponding to pH50 was inferred from the ratio of isolated cDNA inserts corresponding to these different isoforms (pH46:pH50=3:1). Nonetheless, the presence of a polyadenylation signal upstream from the poly A tail in pH50 provided further evidence that it was a bona fide cDNA.

Recombinant Expression of HGF/NK1 in Eukaryotic Expression Systems.

The ORF from pH46 was placed into the MMTneo vector (LaRochelle et al., supra) and introduced into NIH/3T3 cells using standard calcium phosphate transfection methodology. Immunoblot analysis of conditioned medium from transfected cells revealed the presence of a ~20 kD HGF/SF-crossreactive protein that was absent from the medium of control cells. This protein bound avidly to heparin-Sepharose, and eluted under conditions comparable to those employed for HGF/SF (Rubin et al., supra, (1991)). A highly purified preparation was obtained by subsequent sizing chromatography and ion exchange or reverse-phase HPLC. However, as in the case of naturally occurring sources, the amounts recovered were not sufficient to perform extensive biological analysis. As an alternative, we expressed the protein in Sf9 insect cells with a baculovirus vector. A one-step purification process based on heparin affinity chromatography yielded approximately 40 μg of purified material from 1 liter of conditioned medium (FIG. 13).

Biological Activity of Purified, Recombinant HGF/NK1.

In contrast to HGF/SF, HGF/NK1 exhibited modest mitogenic activity as determined by [$^3$H]-thymidine incorporation in B5/589 human mammary epithelial cells (FIG. 14A). At 8 nM, HGF/NK1 stimulated only ~20% of the maximal DNA synthesis elicited by HGF/SF (obtained with 0.5 nM). However, HGF/NK1 exhibited greater mitogenic activity when tested in the presence of insulin or insulin-like growth factor-I. For instance, see FIG. 15, which compares the activity of HGF, HGF/NK1 and HGF/NK2 on B5/589 cells in the presence of insulin.

Figure 14B:
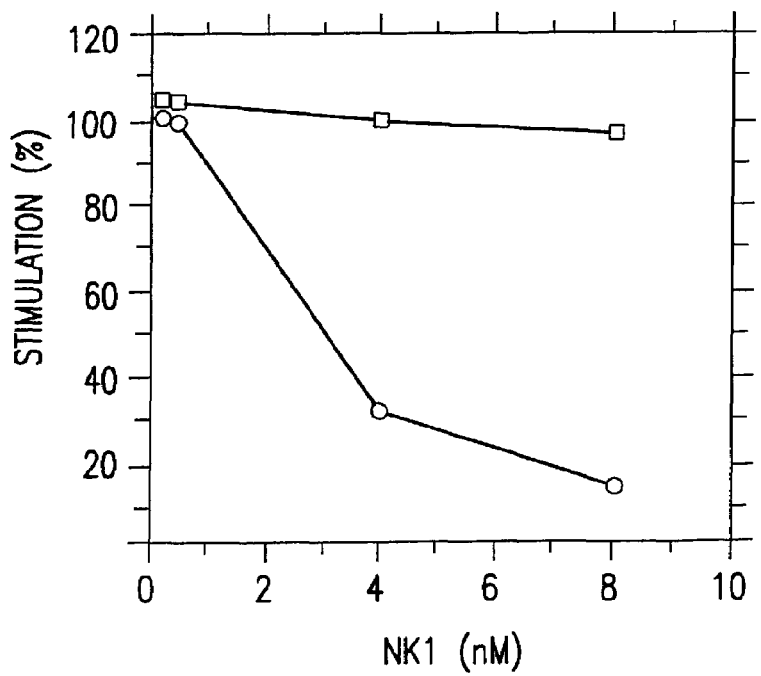

Alternatively, HGF/NK1 behaved as a specific antagonist of HGF/SF in the B5/589 bioassay. A ~20-fold molar excess of HGF/NK1 reduced the mitogenic activity of HGF/SF by ~50%. No inhibition of the stimulatory effect of epidermal growth factor (EGF) was seen, indicating that this effect was specific for HGF/SF (FIG. 14B). At high concentrations (10-20 nM), we detected moderate scattering of MDCK canine kidney cells.

Purified recombinant HGF/NK1 stimulated Met tyrosine phosphorylation and binds directly to Met. To further define its interactions with Met, we tested the ability of exogenously added HGF/NK1 to stimulate Met tyrosine phosphorylation. Using the same concentrations tested in the bioassays described above, we observed that HGF/NK1 triggered Met tyrosine phosphorylation. Combined with the bioassay data, these results indicated there was no simple correlation between Met tyrosine signal intensity and [$^3$H]-thymidine incorporation (FIG. 14).

Crosslinking of [$^{125}$I]-labeled HGF/NK1 to B5/589 cells and subsequent immunoprecipitation with a Met-specific peptide antiserum established that HGF/NK1 binds directly to Met. Crosslinking performed in the presence of either excess unlabeled HGF/NK1 of HGF/SF suggested that the affinity of the truncated molecule for Met was approximately one-fourth that of the full-length factor.

The entire contents of all references cited above are incorporated herein by reference.

* * * *

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A substantially pure Hepatocyte Growth Factor (HGF) variant protein, HGF/NK2, that is a truncated form of HGF comprising the N-terminal and first two kringle domains of HGF, and wherein said HGF/NK2 protein a) has a molecular weight of 34 kD as analyzed on 10% SDS-PAGE under reducing conditions, b) is a competitive antagonist of HGF and c) inhibits HGF-induced mitogenesis, and wherein said HGF/NK2 variant protein does not contain the entire Kringle 3 (K3), Kringle 4 (K4), Linker (L) and serine protease domains of mature HGF.

2. The substantially pure HGF variant of claim 1, comprising the amino acid sequence as shown in SEQ ID NO: 8, wherein said HGF/NK2 variant protein does not contain the entire Kringle 3 (K3), Kringle 4 (K4), Linker (L) and serine protease domains of mature HGF.

3. The substantially pure HGF variant of claim 2, wherein alanine is substituted for cysteine at position 214.

4. A pharmaceutical composition for inhibiting HGF induced mitogenesis in cells expressing the receptor for HGF, said composition comprising the HGF variant of claim 1 and a pharmaceutically acceptable carrier.

5. A substantially pure, naturally occurring Hepatocyte Growth Factor (HGF) variant protein, HGF/NK2, that is a truncated form of HGF consisting of the N-terminal and first two kringle domains of HGF, and wherein said HGF/NK2 protein a) has a molecular weight of 34 kD as analyzed on 10% SDS-PAGE under reducing conditions, b) which is a competitive antagonist of HGF and c) inhibits HGF-induced mitogenesis and wherein said HGF/NK2 protein does not contain the entire Kringle 3 (K3), Kringle 4 (K4), Linker (L) and serine protease domains of mature HGF.

6. A substantially pure, naturally occurring Hepatocyte Growth Factor (HGF) variant protein, HGF/NK2, that is a truncated form of HGF consisting of the N-terminal and first two kringle domains of HGF, wherein said HGF/NK2 protein a) has a molecular weight of 34 kD as analyzed on 10% SDS-PAGE under reducing conditions, b) which is a competitive antagonist of HGF and c) inhibits HGF-induced mitogenesis, wherein said HGF/NK2 protein does not contain the entire Kringle 3 (K3), Kringle 4 (K4), Linker (L) and serine protease domains of mature HGF, and wherein the HGF/NK2 consists of the amino acid sequence as shown in SEQ ID NO: 8.

7. A substantially pure Hepatocyte Growth Factor (HGF) variant that is a truncated form of HGF consisting of the amino acid sequence as shown in SEQ ID NO: 8, and that inhibits HGF-induced mitogenesis.

8. The substantially pure HGF variant of claim 7, wherein alanine is substituted for cysteine at position 214.

9. A substantially pure Hepatocyte Growth Factor (HGF) variant protein, HGF/NK2, that is a truncated form of HGF comprising the N-terminal and first two kringle domains of HGF, wherein said HGF/NK2 protein a) has a molecular weight of 34 kD as analyzed on 10% SDS-PAGE under reducing conditions, b) is a competitive antagonist of HGF and c) inhibits HGF-induced mitogenesis, wherein said HGF/NK2 variant protein does not contain the entire Kringle 3 (K3), Kringle 4 (K4), Linker (L) and serine protease domains of mature HGF, and wherein the HGF/NK2 consists of the amino acid sequence as shown in SEQ ID NO: 8.

* * * * *

UNITED STATES PATENT AND TRADEMARK OFFICE
CERTIFICATE OF CORRECTION

PATENT NO. : 7,605,127 B2  Page 1 of 1
APPLICATION NO. : 10/283769
DATED : October 20, 2009
INVENTOR(S) : Chan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1178 days.

Signed and Sealed this

Fifth Day of October, 2010

David J. Kappos
*Director of the United States Patent and Trademark Office*